(12) United States Patent
Matsunaga

(10) Patent No.: US 6,869,903 B2
(45) Date of Patent: Mar. 22, 2005

(54) SYNTHESIS OF POLYMERIZATION CATALYST COMPONENTS

(75) Inventor: Phillip T. Matsunaga, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 37 days.

(21) Appl. No.: 10/290,122

(22) Filed: Nov. 7, 2002

(65) Prior Publication Data

US 2004/0092387 A1 May 13, 2004

(51) Int. Cl.$^7$ .................................................. C08F 4/64
(52) U.S. Cl. ........................ 502/152; 502/169; 556/53
(58) Field of Search ................................ 502/152, 169; 556/53

(56) References Cited

U.S. PATENT DOCUMENTS

2002/0032287 A1  3/2002  McCullough ................. 526/68
2002/0052446 A1 * 5/2002  Becke et al. ................. 525/192

FOREIGN PATENT DOCUMENTS

| DE | 4332009 A1 | 3/1995 |
| EP | 0 200 351 A2 | 11/1986 |
| EP | 0 705 849 A1 | 4/1996 |
| WO | WO 97/07141 | 2/1997 |

OTHER PUBLICATIONS

Thomas et al., "Zirconocene and rac–[1,2–Ethylene–1,1'bis(tetrahydroindenyl)]zirconium Complexes of 2–Vinylpyridine", Organometallics, 1998, 17, 2096–2102.*
Jordan et al., "Reactive Cationic Dicyclopentadienylzirconium(IV) Complexes", J. Am. Chem. Soc. 1986, 108, 1718–1719.*
William W. Porterfield, *Inorganic Chemistry, A Unified Approach* (1984), pp. 273–274.
Jim. D. Atwood, *Inorganic and Organometallic Reaction Mechanisms* (1985), pp. 63–64; 111–112; 139–140.
W. Kaminsky, et al., *Fluorinated Half–Sandwich Complexes as Catalysts in Syndiospecific Styrene Polymerization*, 30(25) Macromolecules 7647–7650 (1997).
E.F. Murphy, et al., *Synthesis and spectroscopic characterization of a series of substituted cyclopentadienyl Group 4 fluorides; crystal structure of the acetylacetonato complex* [(acac)$_2$($\eta^5$–C$_5$Me$_5$)Zr($\mu$–F)SnMe$_3$Cl], Dalton, 1983 (1996).
Ashby, et al., *The Preparation of Organomagnesium Fluorides by Organometallic Exchange Reactions*, Journal of Organometallic Chemistry, 72 (1974) 11–20.
E.F. Murphy et al. in *Organometallic Fluorides; Compounds Containing Carbon—Metal—Fluorine Fragments of d–Block Metals*, 97 Chem. Rev. 3425–3468 (1997).
Antinolo, et al., *Metallocene Derivatives of Early Transition Elements, Part 4, Sunthesis and Crystal Structures of a Series of Zirconocene(iv) Halides [Zr($\eta$–C$_5$H$_4$SiMe$_3$)$_2$X$_2$] (X=CI or Br) and [Zr{$\eta$–C$_5$H$_3$(SiMe$_3$)$_2$–1,3}$_2$X$_2$] (X=F, Br, or I)*, J. Chem. Soc. Dalton Trans. (1987) 1463–1472.

F. Garbassi, et al., *XPS study of metallocene based catalysts for the polymerization of ethylene*, Journal of Molecular Catalysis A: Chemical 101 199–209 (1995).
A. Herzog, et al., *Reactions of ($\eta^5$–C$_5$Me$_5$)ZrF$_3$, ($\eta^5$–C$_5$Me$_4$Et)ZrF$_3$, ($\eta^5$–C$_5$M4$_5$)$_{22}$ZrF$_2$, ($\eta^5$–C$_5$Me$_5$) HfF$_3$, and($\eta^5$–C$_5$Me$_5$)TaF$_4$ with AlMe$_3$, Structure of the First Hafnium–Aluminum–Carbon Cluster*, 15 ORGANOMETALLICS 909–917 (1996).
P.M. Druce et al. in *Metallocene Halides: Part I. Synthesis, Spectra, and Redistribution Equilibria of Di–$\pi$–cyclopentadienyl–Ti(IV), –Zr(IV), and –Hf(IV)*, 14 J. Chem. Soc. 2106–2110 (1969).
W.W. Lukens, Jr. et al. in *A $\pi$–Donor Spectrochemical Series for X in (Me$_5$C$_5$)$_2$TiX, and $\beta$–Agostic Interactions in X=Et and N(Me)Ph*, 118 J. Am. Chem. Soc. 1729–1728 (1996).
Z. Xie et al., *Synthesis, Molecular Structure, and Reactivity of Organolanthanide Fluoride Complexes, [{(Me$_3$Si)$_2$C$_5$H$_3$}$_2$Ln($\mu$–F)]$_2$ (Ln=La, Nd, Sm, Gd) and [(C$_5$H$_5$)$_2$Ln($\mu$–F) (THF)]$_2$(Ln=Y, Yb)*, 17 ORGANOMETALLICS 3937–3944 (1998).

* cited by examiner

Primary Examiner—Caixia Lu
(74) Attorney, Agent, or Firm—Kevin M. Faulkner

(57) ABSTRACT

The present invention provides a method of synthesizing fluorided metallocene catalyst components comprising contacting at least one fluoriding agent comprising fluorine with one or more alkylated metallocene catalyst components comprising one or more non-halogen leaving groups to produce a fluorided catalyst component; wherein from less than 3 equivalents of fluorine are contacted for every equivalent of leaving group. The method of the invention is exemplified by the following reaction which takes place in a non-coordinating diluent such as pentane:

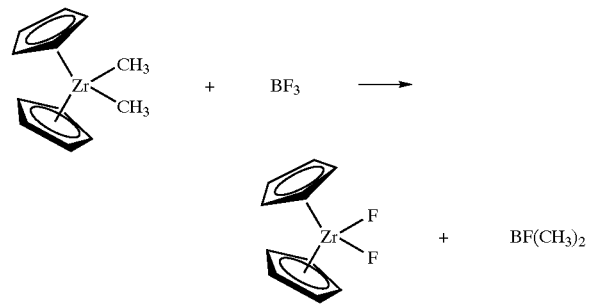

wherein one or both of the "Cp" rings may be substituted with an R group as described herein, and may be bridged. The reaction can be run at any desirable temperature, desirably between 10° C. and 35° C. The reaction product of the BF$_3$ and dimethyl zirconocene is the fluorided zirconocene. The mole ratio of the BF$_3$ fluoriding agent and the starting metallocene is less than 2:1 (fluoriding agent:metallocene) in one embodiment, and less than or equal to 1.6:1 in a particular embodiment, and less than or equal to 1.5:1 in a more particular embodiment, and less than or equal to 1.2:1 in yet a more particular embodiment.

19 Claims, No Drawings

SYNTHESIS OF POLYMERIZATION CATALYST COMPONENTS

FIELD OF THE INVENTION

The present invention relates to a method of synthesizing polymerization catalyst components, and in particular to a method of synthesizing fluorided catalyst components comprising at least one fluoride leaving group, wherein the starting material is one or more alkylated catalyst components.

BACKGROUND OF THE INVENTION

Although much work has been done in olefin polymerization catalysis, there is still a desire to improve the process. In particular, there is a need to provide a practical, commercially viable method of making polyolefins that can utilize the newer "single-site" catalyst components known in the art. There is great interest because, while lab scale processes may afford desirable polymers using, for example, metallocene catalyst components, commercial scale up is often hindered by problems such as reactor fouling. In particular, olefin polymerization reactions catalyzed using single-site catalyst components are often subject to uncontrollable phases, wherein the polymer agglomerates into large (greater than 1 cm) chunks or larger, and can often "sheet" on the inside surface of the reactor, causing, among other problems, a lack of heat removal in the reactor, and further "running away" of the polymerization. In these cases, the reactor must be shut down, resulting in costly delays and lack of commercial viability.

A promising class of single-site catalysts for commercial use includes those wherein the metal center has at least one extractable fluorine (or fluorine "leaving group"). Disclosures of such catalysts include U.S. 20020032287; WO 97/07141; DE 43 32 009 A1; EP-A2 0 200 351; EP-A1 0 705 849; E. F. Murphy, et al., *Synthesis and spectroscopic characterization of a series of substituted cyclopentadienyl Group 4 fluorides; crystal structure of the acetylacetonato complex [(acac)$_2$($\eta^5$-C$_5$Me$_5$)Zr($\mu$-F)SnMe$_3$Cl]*, DALTON, 1983 (1996); A. Herzog, et al., *Reactions of ($\eta^5$-C$_5$Me$_5$) ZrF$_3$, ($\eta^5$-C$_5$Me$_4$Et)ZrF$_3$, ($\eta^5$-C$_5$M4$_5$)$_2$ZrF$_2$, ($\eta^5$-C$_5$Me$_5$) HfF$_3$, and ($\eta^5$-C$_5$Me$_5$)TaF$_4$ with AlMe$_3$, Structure of the First Hafnium-Aluminum-Carbon Cluster*, 15 ORGANOMETALLICS 909–917 (1996); F. Garbassi, et al., JOURNAL OF MOLECULAR CATALYSIS A: CHEMICAL 101 199–209 (1995); and W. Kaminsky, et al., *Fluorinated Half-Sandwich Complexes as Catalysts in Syndiospecific Styrene Polymerization*, 30(25) MACROMOLECULES 7647–7650 (1997). Use of such single site catalyst components in a olefin polymerization system is desirable, especially in gas-phase polyethylene polymerization.

With the growing use of such catalysts, there is a need to provide a practical method of making such catalysts. Typically, the production of the fluorine-containing catalyst component, or "fluorided" catalyst component, entails the reaction of a fluoriding agent with the corresponding "chlorided" catalyst component. The use of some common fluoriding agents presents many challenges, excessive cost among them. Other methods of fluoriding metallocene catalyst components are disclosed by Z. Xie et al., *Synthesis, Molecular Structure, and Reactivity of Organolanthanide Fluoride Complexes, [{(Me$_3$Si)$_2$C$_5$H$_3$}$_2$Ln($\mu$-F)]$_2$ (Ln=La, Nd, Sm, Gd) and [(C$_5$H$_5$)$_2$Ln($\mu$-F)(THF)]$_2$ (Ln=Y, Yb)*, 17 ORGANOMETALLICS 3937–3944 (1998); E. F. Murphy et al. in *Organometallic Fluorides: Compounds Containing Carbon-Metal-Fluorine Fragments of d-Block Metals*, 97 CHEM. REV. 3425–3468 (1997); W. W. Lukens, Jr. et al. in *A $\pi$-Donor Spectrochemical Series for X in (Me$_5$C$_5$)$_2$TiX, and $\beta$-Agostic Interactions in X=Et and N(Me)Ph*, 118 J. AM. CHEM. SOC. 1729–1728 (1996); and P. M. Druce et al. in *Metallocene Halides: Part I. Synthesis, Spectra, and Redistribution Equilibria of Di-$\pi$-cyclopentadienyl-Ti(IV), -Zr (IV), and -Hf(IV)*, 14 J. CHEM. SOC. 2106–2110 (1969). However, these methods fall short of a desirable, cost effective commercial method of making fluorided metallocene catalyst components. What is needed is an improved method of producing fluorided catalyst components that will be more practical and beneficial to commercial olefin polymerization and oligomerization processes. The present invention is directed towards this improvement.

SUMMARY OF THE INVENTION

The present invention solves these and other problems by providing a method of making a fluorided catalyst component comprising contacting at least one fluoriding agent comprising fluorine with one or more alkylated metallocene catalyst components comprising one or more non-halogen leaving groups to produce a fluorided catalyst component; wherein from less than 3 equivalents of fluorine are contacted for every equivalent of leaving group. The method of the invention is exemplified by the following reaction which takes place in a non-coordinating diluent such as pentane:

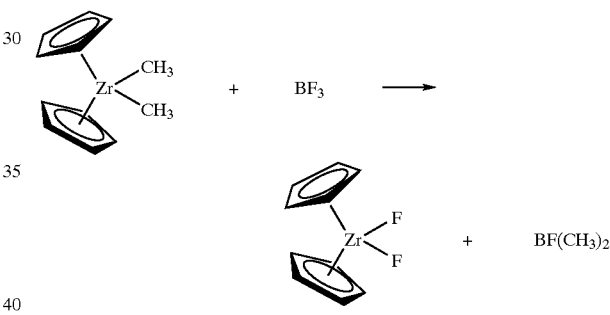

wherein one or both of the "Cp" rings may be substituted with an R group as described herein, and may be bridged. The reaction can be run at any desirable temperature, desirably between 10° C. and 35° C. The reaction product of the BF$_3$ and dimethyl zirconocene is the fluorided zirconocene. The mole ratio of the BF$_3$ fluoriding agent and the starting metallocene is less than 2:1 (fluoriding agent:metallocene) in one embodiment, and less than or equal to 1.6:1 in a particular embodiment, and less than or equal to 1.5:1 in a more particular embodiment, and less than or equal to 1.2:1 in yet a more particular embodiment. The method of the invention is an improvement over the prior art in allowing for full fluorination of a metallocene metal center without use of excess fluoriding agent, as well as allowing for full fluorination without increasing or decreasing the reaction temperature (relative to ambient temperature), both parameters of which influence costs in bulk production of the fluorided metallocene catalyst component.

DETAILED DESCRIPTION OF THE INVENTION

General Definitions

As used herein, the phrase "catalyst system" includes at least one "catalyst component" and at least one "activator", both of which are described further herein. The catalyst system may also include other components, such as supports, etc., and is not limited to the catalyst component and/or activator alone or in combination. The catalyst system may include any number of catalyst components in any combination as described herein, as well as any activator in any combination as described herein.

As used herein, the phrase "catalyst component" includes any compound, in the presence of an activator, capable of catalyzing the polymerization or oligomerization of olefins; wherein the catalyst component comprises at least one Group 3 to Group 12 atom ("metal center"), and at least one leaving group bound thereto. In one embodiment, the catalyst component is selected from any one or more metallocene catalyst components as described herein.

As used herein, the phrase "leaving group" refers to one or more chemical moieties bound to the metal center of the catalyst component that can be abstracted from the catalyst component by an activator, thus producing the species active towards olefin polymerization or oligomerization. The activator is described further below.

As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press $81^{st}$ ed. 2000).

As used herein, a "hydrocarbyl" includes aliphatic, cyclic, olefinic, acetylenic and aromatic radicals (i.e., hydrocarbon radicals) comprising hydrogen and carbon that are deficient by one hydrogen. A "hydrocarbylene" is deficient by two hydrogens.

As used herein, an "alkyl" includes linear, branched and cyclic paraffin radicals that are deficient by one hydrogen. Thus, for example, a $-CH_3$ group ("methyl") and a $CH_3CH_2-$ group ("ethyl") are examples of alkyls.

As used herein, an "alkenyl" includes linear, branched and cyclic olefin radicals that are deficient by one hydrogen; alkynyl radicals include linear, branched and cyclic acetylene radicals deficient by one hydrogen radical.

As used herein, "aryl" groups includes phenyl, naphthyl, pyridyl and other radicals whose molecules have the ring structure characteristic of benzene, naphthylene, phenanthrene, anthracene, etc. For example, a $C_6H_5^-$ aromatic structure is an "phenyl", a $C_6H_4^{2-}$ aromatic structure is an "phenylene". An "arylalkyl" group is an alkyl group having an aryl group pendant therefrom; an "alkylaryl" is an aryl group having an alkyl group pendant therefrom.

As used herein, an "alkylene" includes linear, branched and cyclic hydrocarbon radicals deficient by two hydrogens. Thus, $-CH_2-$ ("methylene") and $-CH_2CH_2-$ ("ethylene") are examples of alkylene groups. Other groups deficient by two hydrogen radicals include "arylene" and "alkenylene".

As used herein, the phrase "heteroatom" includes any atom other than carbon and hydrogen that can be bound to carbon. A "heteroatom-containing group" is a hydrocarbon radical that contains a heteroatom and may contain one or more of the same or different heteroatoms. Non-limiting examples of heteroatom-containing groups include radicals of imines, amines, oxides, phosphines, ethers, ketones, oxoazolines heterocyclics, oxazolines, thioethers, and the like.

As used herein, an "alkylcarboxylate", "arylcarboxylate", and "alkylarylcarboxylate" is an alkyl, aryl, and alkylaryl, respectively, that possesses a carboxyl group in any position. Examples include $C_6H_5CH_2C(O)O^-$, $CH_3C(O)O^-$, etc.

As used herein, the term "substituted" means that the group following that term possesses at least one moiety in place of one or more hydrogens in any position, the moieties selected from such groups as halogen radicals (esp., Cl, F, Br), hydroxyl groups, carbonyl groups, carboxyl groups, amine groups, phosphine groups, $C_1$ to $C_{10}$ alkoxy groups, phenyl groups, naphthyl groups, $C_1$ to $C_{10}$ alkyl groups, $C_2$ to $C_{10}$ alkenyl groups, and combinations thereof Examples of substituted alkyls and aryls includes, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbamoyl radicals, alkyl- and dialkyl-carbamoyl radicals, acyloxy radicals, acylamino radicals, arylamino radicals, and combinations thereof.

As used herein, structural formulas are employed as is commonly understood in the chemical arts; lines ("—") used to represent associations between a metal atom ("M", Group 3 to Group 12 atoms) and a ligand or ligand atom (e.g., cyclopentadienyl, nitrogen, oxygen, halogen ions, alkyl, etc.), as well as the phrases "associated with", "bonded to" and "bonding", are not limited to representing a certain type of chemical bond, as these lines and phrases are meant to represent a "chemical bond"; a "chemical bond" defined as an attractive force between atoms that is strong enough to permit the combined aggregate to function as a unit, or "compound".

A certain stereochemistry for a given structure or part of a structure should not be implied unless so stated for a given structure or apparent by use of commonly used bonding symbols such as by dashed lines and/or heavy lines.

Unless stated otherwise, no embodiment of the present invention is herein limited to the oxidation state of the metal atom "M" as defined below in the individual descriptions and examples that follow.

Method of Fluoriding an Alkylated Catalyst Component

One aspect of the present invention includes a method of synthesizing fluorided catalyst components. The "fluorided catalyst component" is one that comprises at least one fluoride chemically bonded to the Group 3 to Group 12 atom (or "metal center") of the catalyst component. Another aspect of the invention includes the use of such fluorided catalyst components as part of a catalyst system to oligomerize and/or polymerize olefins to form such polymers as homopolymers and copolymers of polyethylene and polypropylene.

In one embodiment of the invention, the synthesis of the fluorided catalyst components includes contacting at least one fluoriding agent with at least one alkylated catalyst component in the presence of a non-coordinating diluent. In another embodiment of the invention, the synthesis of the fluorided catalyst components includes first alkylating one or more catalyst components, followed by contacting at least one fluoriding agent with the one or more alkylated catalyst components in a non-coordinating diluent.

As used herein, "alkylated catalyst component" refers to a catalyst component that comprises at least one non-halogen (Group 17 atom) leaving group; and more particularly a leaving group that provides for at least one bond between the metal of the catalyst component and an atom selected from Group 12 to Group 16 atoms; and leaving groups that provide for at least one bond between the metal of the catalyst component and an atom selected from boron, aluminum, carbon, silicon, nitrogen, phosphorous, oxygen and sulfur in yet a more particular embodiment; and leaving groups that provide for one carbon bonded directly to the metal of the catalyst component in yet a more particular embodiment. More particularly, alkylated catalyst components useful in the present invention are those wherein one or more of the X groups in structures (I) through (VI) are selected from hydrocarbons and heteroatom containing hydrocarbons as described further below. The term "alkylated" in association with the "catalyst component" is not limited to catalyst components bound only to alkyl groups (as defined above), but is meant to include all hydrocarbon and heteroatom containing hydrocarbons that provide at least one non-halogen atom—metal bond per group.

The "fluorided catalyst component" is defined above, and may be more particularly defined by the formulas/structures (I) through (VI) wherein one or more of the X groups are a fluoride ion.

The "fluoriding agent" is a compound or combination of compounds capable of forming a chemical bond between at least one fluorine atom and the metal center of an alkylated catalyst component. Desirably, the fluoriding agent is a compound or combination of compounds that is soluble in a non-coordinating diluent, as described below, and comprises at least one fluorine atom. In a particular embodiment, the fluoriding agent is selected from compounds comprising at least one fluorine atom, at least two fluorine atoms in a particular embodiment, and one or more atoms selected from H, Li, Na, K, Ca, Ti, Zr, Sm, Nb, Ta, Mo, B, Al, Ga, Ge, Re, C, Si, Sn, N, P, O, S, Cl, I and Br. Even more particularly, the fluoriding agent is selected from compounds comprising at least one fluorine atom, at least two fluorine atoms in a particular embodiment, and one or more atoms selected from the group consisting of H, Li, Na, K, B, Al, Ga, C, Si, N, P, O, S, Cl, I and Br. And even more particularly, the fluoriding agent is selected from compounds comprising at least one fluorine atom, at least two fluorine atoms in a particular embodiment, and one or more atoms selected from the group consisting of H, Li, Na, K, B, C, Si, N, P, O, S, Cl, I and Br. And even more particularly, the fluoriding agent is selected from compounds comprising at least one fluorine atom, at least two fluorine atoms in a particular embodiment, and one or more atoms selected from the group consisting of Li, Na, K, B, C, Si, N, P, O, S, Cl, I and Br. And even more particularly, the fluoriding agent is selected from compounds comprising at least one fluorine atom, at least two fluorine atoms in a particular embodiment, at least one boron atom and one or more atoms selected from the group consisting of H, Li, Na, K, C, Si, N, P, O, S, Cl, I and Br. The combination of at least two fluorine atoms and other atoms described above are arranged to form a chemical compound in such a manner that is consistent with known bonding schemes for such atoms.

In one embodiment of the invention, tin-based fluoriding agents are substantially absent, meaning they are not deliberately added, nor present to any detectable extent, in the fluoriding step of the invention. Tin-based fluoriding agents include compounds that consist of tin and atoms selected from hydrogen, chloride ions, fluoride ions, carbon and combinations thereof. Examples of tin-based fluoriding agents include $SnF_2$, $SnF_4$, and $Sn(CH_3)_3F$. In yet another embodiment, fluoriding agents comprising HF are substantially absent.

Non-limiting examples of fluoriding agents are selected from $Et_4NPF_6$, $(NH_4)_2SiF_6$, $NH_4PF_6$, $NH_4F$, $NH_4F_2$, $(NH_4)_2TaF_7$, $NH_4NbF_4$, $SnF_4$ and its alkylated derivatives (e.g., $[CH_3]_3SnF$) $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_5$, $BrF_5$, $IF_7$, $NF_3$, $NHF_2$, $CH_3NHF$, $NH_4HF_2$, $NH_4BF_4$, $BF_3$, and other boron-fluoride compounds, and mixtures thereof. More particularly, suitable fluoriding agents may be selected from $Et_4NPF_6$, $NH_4PF_6$, $(NH_4)_2SiF_6$, $NH_4F$, $NH_4F_2$, $(NH_4)_2TiF_6$, $(NH_4)_2ZrF_6$, $SO_2ClF$, $F_2$, NaF, $SiF_4$, $SF_6$, $ClF_3$, $ClF_5$, $BrF_5$, $IF_7$, $NF_3$, HF, $NHF_2$, $NH_4HF_2$, $NH_4BF_4$, $BF_3$, and other boron-fluoride compounds, and mixtures thereof. These compounds also exemplify various embodiments of the two or more fluorine atoms with various atoms listed above.

In yet a more particular embodiment, the fluoriding agent is selected from Group 13 fluoride compounds. The "Group 13 fluoride compound" is any compound comprising at least one Group 13 atom and at least one fluoride ion. Examples of such compounds include boron mono-, di- and trifluoride compounds, aluminum mono-, di- and trifluoride compounds, gallium mono-, di- and trifluoride compounds, and alkylated and/or halogenated (Cl, Br, I) derivatives thereof, as well as dimers, trimers, and oligomers thereof of these compounds. And in a more particular embodiment, the fluoriding agent is selected from boron-fluoride compounds which include compounds having the general formula $(BF_yR_{3-y})_z$, wherein y ranges from 1 to 3; and z ranges from 1 to 20 in one embodiment, and from 1 to 5 in another embodiment, and is 1 in a more particular embodiment; and wherein R is selected from hydride, chloride, bromide, $C_1$ to $C_{10}$ alkyls, substituted $C_1$ to $C_{10}$ alkyls, $C_1$ to $C_{10}$ alkoxys, $C_6$ to $C_{12}$ aryls, $C_6$ to $C_{12}$ aryloxys and substituted $C_6$ to $C_{12}$ aryls. In a more particular embodiment, the Group 13 fluoride compound is $BF_3$. The invention is not herein limited to the physical state of the fluoriding agent, as it may be a liquid, solid, suspension in a diluent, and/or may be coordinated to another compound such as, for example, an ether, water, or other coordinating group such as these compounds are commercially provided.

In any case, the fluorided catalyst components are obtained, in one embodiment, by contacting the alkylated catalyst component and fluoriding agent in a non-coordinating diluent. In a particular embodiment, the fluorided catalyst components are obtained by contacting the fluoriding agent with the alkylated catalyst component directly, without the addition of a diluent to either the fluoriding agent or alkylated catalyst component. In yet another embodiment, the fluoriding component is added directly, without dilution in a diluent, into the alkylated catalyst component which is present in a non-coordinating diluent. By "contacting", it is meant that the components are added together, in the presence of a diluent in one embodiment, under conditions that favor a reaction between the fluoriding agent and the alkylated catalyst component that will produce a chemical bond between a fluorine atom and the metal center of the catalyst component.

The non-coordinating diluent is any substance or mixture of substances that excludes chemical moieties that are capable of forming a chemical bond or ionic interaction with the alkylated olefin polymerization catalyst. Desirably, the non-coordinating diluent is one that is in a liquid state at the temperature at which the components are contacted with one another to affect the formation of a bond between at least one fluorine and the catalyst component. In one embodiment, the non-coordinating diluent is a liquid at between −30° C. and 200° C. at or near atmospheric pressure in one embodiment, and between −10° C. and 100° C. at or near atmospheric pressure in another embodiment.

In a particular embodiment, the non-coordinating diluent is a hydrocarbon diluent consisting of carbon and hydrogen. In another embodiment, the diluent may also include chlorinated hydrocarbons such as methylene chloride, trichloromethane, dichloroethane, etc. In a more particular embodiment, the non-coordinating diluent is selected from the group consisting of $C_4$ to $C_{40}$ linear alkanes, branched alkanes, cyclic alkanes, $C_6$ to $C_{20}$ aromatic hydrocarbons, and mixtures thereof. In yet a more particular embodiment, the non-coordinating diluent is selected from the group consisting of butane, pentane, hexane, heptane, octane, cyclohexane, benzene, ethylbenzene, toluene, xylene, naphthylene, isomers of each, and mixtures thereof.

A general reaction scheme for the synthesis of fluorided catalyst components of the invention can include step (b) alone, wherein the alkylated catalyst component is a starting material, or alternatively, can include steps (a) and (b) as follows:

  (a)

  (b)

wherein "C" is the catalyst component, "AA" is an alkylating agent, "AC" is an alkylated catalyst component, "FA" is the fluoriding agent, and "FC" is the fluorided catalyst component; X is the number of equivalents of AA; and Y is the number of equivalents of FA;

the value of X is a number, including fractional numbers, ranging from 0.5 to 5 in one embodiment; and ranging from 0.8 to 5 in another embodiment, and ranging from 1 to 2 in yet a more particular embodiment; and X is 2 in yet another embodiment; and the value of Y is a number, including fractional numbers, ranging from 0.1 to less than 3 in one embodiment; and ranging from 0.8 to less than 2.5 in another embodiment, and ranging from 1 to less than 2 in yet a more particular embodiment, and ranging from 0.6 to 1.8 in yet a more particular embodiment, and ranging from 0.8 to 1.5 in yet a more particular embodiment, and ranging from 0.9 and 1.2 in yet a more particular embodiment, wherein the equivalents are based on the equivalents of the entire fluoriding agent compound.

The alkylating agent in (a) is any agent or combination of agents capable of forming one or more non-halogen—metal bonds between the metal center catalyst component and hydrocarbon or heteroatom containing group (e.g., alkyls, aryls, etc.), and in particular, capable of forming a bond between the hydrocarbon group or heteroatom containing hydrocarbon group and the Group 3 to Group 12 metal center of the catalyst component. In a particular embodiment, the alkylating agent is selected from $C_1$ to $C_6$ alkyl Group 1 compounds, $C_1$ to $C_6$ alkyl Group 2 compounds, $C_6$ to $C_{12}$ aryl Group 1 compounds, $C_6$ to $C_{12}$ aryl Group 2 compounds, aluminum alkyl compounds, and mixtures thereof, these compounds being capable of forming a carbon—metal bond. Examples of such compounds include triethylaluminum ("TEAL") and other methyl/ethyl aluminum derivatives; Grignard Reagents such as methylmagnesium bromide and phenylmagnesium bromide and other Grignard agents having the general formula $R^G$Mg (halogen), wherein the $R^G$ group is any alkyl or aryl group such as is defined for the X groups associated with the alkylated catalyst components; and lithium and sodium alkyl compounds. These compounds can be purchased or produced by techniques common in the chemical arts. Other alkylating agents capable of forming, for example, alkoxy linkages to the metal center are common in the art, such as Group 1 or Group 2 alkoxy reagents; and as disclosed by, for example, W. W. Lukens, Jr. et al., 118 J. AM. CHEM. SOC. 1729–1728 (1996) (methods of adding alkyls, alkoxys, amines leaving groups to metallocenes).

In one embodiment, step (a), or the alkylation step, takes place in a diluent having a dielectric constant greater than 2.0 at 20° C. and a boiling point of less than 100° C., less than 60° C. in a particular embodiment. Described another way, the contacting step (a) takes place in a diluent selected from $C_1$ to $C_{20}$ heteroatom containing hydrocarbons; wherein the heteroatom is selected from oxygen, sulfur, phosphorous, nitrogen, fluorine, chlorine, and bromine. Non-limiting examples of useful diluents include diethylether, tetrahydrofuran, DMSO, and other ethers and ketones. In a particular embodiment, the diluent used in (a) is one that can be easily removed under vacuum (from 1 to $1 \times 10^{-6}$ torr) and/or gentle heating (less than 100° C.) such that the AC product can be easily isolated. The reaction may take place from 1 min. to 24 hours at any temperature desirable to afford the maximum yield of mono-, di-, or mixed alkylated product, from −10° C. to 40° C. in one embodiment. The reaction can be monitored by techniques common in the art to determine a desirable stopping point.

In a particular embodiment, the AC produced in step (a) above is isolated prior to contacting with a fluoriding agent. The isolated product AC may be in any form, typically a solid. This isolated AC, either synthesized as described herein or obtained in another fashion, may be further purified such as by extraction with a diluent selected from alkanes and aromatic hydrocarbons, desirably such diluents as pentane, hexane, cyclohexane and toluene.

In the fluoriding step, or step (b), it is desirable to contact the reactants in a non-coordinating diluent as described above. The reaction can be performed at any desirable temperature to afford the highest yield of desired products, as the reaction may be monitored by techniques common in the art; example temperature ranges are from −30° C. to 140° C. in one embodiment (or, for example, the reflux temperature of the hydrocarbon solvent such as toluene), and from 0° C. to 50° C. in a particular embodiment, and from 10° C. to 35° C. in yet a more particular embodiment, and from 15° C. to 30° C. in yet a more particular embodiment. In one aspect of the invention, the improved method of making the fluorided metallocene is characterized in the lack of temperature control. Thus, in a particular embodiment, there is no external temperature control exerted on the system such as to significantly increase or decrease the temperature from ambient temperature. By "significant", it is meant that the temperature of the fluoriding reaction is not decreased or increased by more than 5° C.

In a particular embodiment, it is desirable to choose a diluent for the fluoriding step such that the FC product will form a precipitate. The precipitate, or reaction product, may be extracted (or "washed") with any desirable volume of a hydrocarbon diluent to further isolate and purify the fluorided catalyst component. The diluent used to wash the reaction product solid may be at any desirable temperature to remove undesirable side products of the fluoriding reaction, at less than 80° C. in one embodiment. In step (b), the fluoriding step, the AC and FA may be at any concentration that will afford the highest yield using a given diluent. In one embodiment, the AC and FA are independently present in the diluent from up to 10 M (molar) in concentration, and from 1 μM to 2 M in a particular embodiment, and from 1 mM to 1 M in a more particular embodiment, and from 10 mM to 0.5 M in yet a more particular embodiment.

In a particular embodiment, diluents comprising groups selected from non-conjugated carbon-carbon double bonds, oxygen, sulfur, phosphorous, halogens, Group 1 to Group 12 atoms, lanthanide Group atoms, and actinide Group atoms and any combination thereof are substantially absent in the fluoriding step, or (b) above. By substantially absent, it is meant that these diluents are not deliberately added, and particularly, are present, if at all, to an extent no greater than the concentration of the fluoriding agent in the fluoridation step.

A more particular representation of the fluoriding step of the invention is represented by (c):

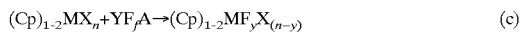 (c)

wherein $(Cp)_{1-2}MX_n$ is an alkylated metallocene catalyst component having n number of non-halogen leaving groups X; Cp is cyclopentadienyl or ligands isolobal to cyclopentadienyl, one or both of which may be substituted; each Cp is bound to M; M is the metal center of the catalyst component and each of X and F (fluoride ion), when present, are chemically bonded to M; n is an integer from 1 to 3;

Y is a number, including fractional numbers, from 0.1 to 3, and represents the number of equivalents of the compound "$F_fA$" as a whole;

$F_fA$ is the fluoriding agent having f number of fluorine atoms per molecule of fluoriding agent, wherein f is an integer from 1 to 6 in one embodiment, and from 2 to 6 in another embodiment; F is a fluoride ion; and $(Cp)_{1-2}MF_yX_{(n-y)}$ is the fluorided metallocene catalyst component; and y is an integer from 1 to 3.

The value of Y in reaction scheme (c), as in (b), is any number, including fractional numbers, less than 2, or 1.9, or 1.8, or 1.7, or 1.6, or 1.5, or 1.4, or 1.3, or 1.2, or 1.1, and greater than 0.3, or 0.4, or 0.5, or 0.6, or 0.7, or 0.8, or 0.9; wherein Y represents the equivalents of the entire fluoriding agent.

The total equivalents of fluorine (as part of the fluoriding agent) is the value of Y multiplied by the value of f. In the method of the present invention, the total equivalents of fluorine per equivalent of non-halogen leaving group X provided by the fluoriding agent is less than 3 in one embodiment, and less than or equal to 2.5 in a more particular embodiment, and less than or equal to 2 in a more particular embodiment, and less than or equal to 1.5 in yet a more particular embodiment. In another aspect of the invention, the total equivalents of fluorine per equivalent of non-halogen leaving group X is any number, including fractional numbers, less than 3, or less than or equal to 2.8, or 2.5, or 2.2, or 2.0, or 1.8, or 1.5, or 1.4, or 1.3, or 1.2, or 1.1, and greater than or equal to 1.

In one aspect of the invention, each X (in scheme (c) and in formula/structures (I) through (VI) infra) is independently selected from: any non-halogen leaving group wherein the atom bonded to the metal is selected from hydride, Group 12 to Group 16 atoms in one embodiment; hydride, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, hydride, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, methyl, phenyl, phenoxy, benzoxy, tosyl, fluoromethyls and fluorophenyls in yet a more particular embodiment; and even more particularly, each X is independently selected from groups that provide for one bond between a carbon of the group and the metal center of the metallocene, thus forming an carbon—metal bond, such groups consisting of $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_6$ to $C_{12}$ heteroatom-containing aryls and $C_1$ to $C_{12}$ heteroatom-containing alkylaryls; the group consisting of $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; and the group consisting of methyl, ethyl, propyl, phenyl, methylphenyl, dimethylphenyl, trimethylphenyl, fluoromethyls (mono-, di- and trifluoromethyls) and fluorophenyls (mono-, di-, tri, tetra- and pentafluorophenyls) in yet a more particular embodiment.

In a particular embodiment of scheme (c), f is 3, n is 2, Y is less than 2, and y is 2; wherein n=y in a desirable embodiment. In another embodiment, f is 3, n is 2, Y is 1 or less than 1, and y is 2. In yet another embodiment, f is 3, n is 1, Y is less than 1, and y is 1. Thus, the present invention provides for a method of replacing at least two alkyl group (non-halogen groups) with two fluorine groups while using less than 2 equivalents of fluoriding agent.

Stated yet another way, the method of the present invention allows for the addition of from 0.6 to 2.5 equivalents of fluorine (as part of the fluoriding agent) for every equivalent of non-halogen leaving group bound to the metal center of the alkylated catalyst component in one embodiment, and from 0.8 to 2.0 equivalents of fluorine (as part of the fluoriding agent) for every equivalent of non-halogen leaving group bound to the metal center of the alkylated catalyst component in another embodiment; and from 0.8 to 1.5 equivalents of fluorine (as part of the fluoriding agent) for every equivalent of non-halogen leaving group bound to the metal center of the alkylated catalyst component in yet a more particular embodiment.

As an example, the alkylated catalyst component may be such a compound as a metallocene wherein two X groups are methyl groups. Once the fluorination process is carried out as described above, the fluorided catalyst component is the corresponding metallocene wherein one or both X groups are fluorides, depending upon the number of equivalents of the fluoriding agent are contacted with the alkylated catalyst component. In one embodiment, less than 2 equivalents of fluoriding agent are added to replace both methyl groups with fluorine ions. If only one X is substituted with fluoride, the other X is the starting methyl group.

In embodiments of the fluoriding step wherein the fluoriding agent is immiscible or only partially miscible with the diluent, it is within the scope of the invention to use a reagent that will assist the transport of the fluoriding agent to the alkylated catalyst component or the diluent phase in which the alkylated catalyst component exists, or assist in the reaction between the fluoriding agent and alkylated catalyst component. Such reagents—phase-transfer catalysts—are known in the art and are used in reactions wherein, for example, an aqueous or polar diluent phase is in contact with a non-polar or hydrocarbon diluent phase, and the reactants are separated as such. Non-limiting examples of such phase-transfer catalysts include quaternary ammonium salts (e.g., quaternary ammonium bisulfate), crown ethers, and others common in the art.

The invention as described herein also includes a method of producing polyolefins comprising the steps of first contacting at least one fluoriding agent with one or more alkylated catalyst components to produce a fluorided catalyst component; followed by contacting the fluorided catalyst component with an activator and olefins selected from $C_2$ to $C_{12}$ olefins under polymerization conditions to produce a polyolefin. The fluorided catalyst component may thus be part of a catalyst system used to oligomerize or polymerize olefins. Methods of polymerization, and common polymerization conditions, are described further herein.

Thus, the present invention may be described by any combination of any of the embodiments or particular embodiments herein presented.

In one aspect, the invention is a method of making a fluorided metallocene catalyst component comprising contacting at least one fluoriding agent comprising fluorine with one or more alkylated metallocene catalyst components comprising one or more non-halogen leaving groups to produce a fluorided catalyst component; wherein from less than 3 equivalents of fluorine are contacted for every equivalent of leaving group. When stating that "from less than 3 equivalents of fluorine are contacted", it should be understood that this refers to 3 equivalents (or other number of equivalents) of fluorine as provided by the fluoriding agent of the invention. In another embodiment, less than or equal to 2.5 equivalents of fluorine are contacted per equivalent of leaving group. In yet another embodiment, less than or equal to 2 equivalents of fluorine are contacted per equivalent of leaving group, and in yet another more particular embodiment, less than or equal to 1.5 equivalents of fluorine are contacted per equivalent of leaving group, and in yet a more particular embodiment, less than or equal to 1.2 equivalents of fluorine are contacted with the alkylated catalyst component per equivalent of non-halogen leaving group bound to the catalyst component.

The fluoriding agent is a compound or combination of compounds capable of forming a chemical bond between at least one fluorine atom and the metal center of an alkylated catalyst component in one embodiment. The fluoriding agent is selected from compounds comprising at least one atom of fluorine and one or more atoms selected from the group consisting of H, Li, Na, K, Ca, Ti, Zr, Sm, Nb, Ta, Mo, B, Al, Ga, Ge, Re, C, Si, Sn, N, P, O, S, F, Cl, I and Br in another embodiment. Described another way, the fluoriding agent is selected from compounds comprising at least one atom of fluorine and one or more atoms selected from the group consisting of H, Li, Na, K, B, C, Si, N, P, O, S, F, Cl, I and Br in yet another embodiment. The fluoriding agent is selected from Group 13 fluoride compounds in a more particular embodiment. And in yet a more particular embodiment, fluoriding agent is selected from boron-fluoride compounds.

The fluoriding agent is contacted with the alkylated catalyst component to produce a fluorided catalyst component, or reaction product, which may include other by-products of the fluoriding reaction. The reaction product may be extracted with a hydrocarbon solvent at from less than 80° C. to yield the fluorided catalyst component in one embodiment, and extracted at a temperature of less than 70° C. in another embodiment, and extracted at a temperature of less than 60° C. in yet a more particular embodiment to further isolate the pure fluorided catalyst component. In one embodiment, the fluoriding agent is added as a neat composition. By "neat composition", it is meant that the fluoriding agent is not diluted, suspended or solublized in a diluent such that more than 2 equivalents of diluent exist per equivalent of fluoriding agent; or alternately, the neat composition is one wherein no other diluent is added.

The fluoriding agent and alkylated catalyst component are contacted in a non-coordinating diluent. The non-coordinating diluent is a hydrocarbon diluent consisting essentially of carbon and hydrogen in one embodiment. The non-coordinating diluent is selected from the group consisting of $C_4$ to $C_{40}$ linear alkanes, branched alkanes, cyclic alkanes, $C_6$ to $C_{20}$ aromatic hydrocarbons and mixtures thereof in another embodiment. In yet another embodiment, non-coordinating diluent is selected from the group consisting of butane, pentane, hexane, heptane, cyclohexane, benzene, toluene, xylene, naphthylene, isomers of each, and mixtures thereof.

The alkylated metallocene catalyst component is selected from alkylated Group 4, 5 and 6 mono- and bis-cyclopentadienyl-type metallocene catalyst components in one embodiment, and can be described as possessing at least one leaving group X. These leaving groups "X" are referred to throughout the specification and claims. In one embodiment, X is independently selected from any non-halogen leaving group. In another embodiment, X is independently selected from groups that provide for at least one bond between the metal center of the alkylated catalyst component and one or more of the group selected from Group 12 atoms, Group 13 atoms, Group 14 atoms, Group 15 atoms, and Group 16 atoms. In yet another embodiment, X is independently selected from the group consisting of $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_5$ to $C_{12}$ heteroatom-containing aryls and $C_6$ to $C_{12}$ heteroatom-containing alkylaryls. In one embodiment, the alkylated catalyst component comprises two leaving groups X.

The components are contacted at a temperature between 0° C. and 60° C. in one embodiment, and between 10° C. and 35° C. in a more particular embodiment, and between 15° C. and 30° C. in yet a more particular embodiment.

Metallocene Catalyst Component

The catalyst system useful in the present invention includes at least one metallocene catalyst component as described herein. The class of so called metallocene catalyst compounds are described throughout in, for example, 1 & 2 METALLOCENE-BASED POLYOLEFINS (John Scheirs & W. Kaminsky eds., John Wiley & Sons, Ltd. 2000), and in particular, for use in the synthesis of polyethylene in 1 METALLOCENE-BASED POLYOLEFINS 261–377 (2000). Alkylated and/or fluorided metallocene catalyst components as described herein include half and full "sandwich" metallocene compounds having one or more Cp (cyclopentadienyl and ligands isolobal to cyclopentadienyl) ligands bonded to at least one Group 3 to Group 12 metal atom, and one or more leaving group(s) bonded to the at least the one metal atom. Hereinafter, these compounds will be referred to as "metallocenes" or "metallocene catalyst components", and may be "alkylated" and/or "fluorided", depending upon the identity of the leaving group "X".

The Cp ligands are generally represented by one or more π-bonded, and/or fused ring(s) or ring systems. In these ligands, the ring(s) or ring system(s) typically comprise atoms selected from Groups 13 to 16 atoms, and more particularly, the atoms that make up the Cp ligands are selected from carbon, nitrogen, oxygen, silicon, sulfur, phosphorous, germanium, boron and aluminum and a combination thereof. Even more particularly, the Cp ligand(s) are selected from cyclopentadienyl ligands and ligands isolobal to cyclopentadienyl, non-limiting examples of which include cyclopentadienyl, tetrahydroindenyl, indenyl, fluorenyl and other structures. Examples of other Cp ligands include structures such as a pentadiene, cyclooctatetraenyl and imide compounds.

The atom M of the metallocene catalyst component may be selected from Groups 3 through 12 atoms, and lanthanide Series atoms in one embodiment; and selected from Groups 3 through 6 in a more particular embodiment, and selected from Groups 4, 5 and 6 in yet a more particular embodiment, and a Group 4 metal in yet a more particular embodiment; and selected from Ti, Zr and Hf in yet a more particular embodiment; and selected from Zr and Hf in yet a more particular embodiment. The Cp ligand(s) form at least one chemical bond with the metal atom M to form the "metallocene catalyst component". The Cp ligands are distinct from the leaving groups bound to the catalyst component in that they are not highly susceptible to substitution reactions.

In one aspect of the invention, the one or more metallocene catalyst components of the invention are represented by the formula (I):

$$Cp^A Cp^B MX_n \quad (I)$$

wherein M is as defined above; each X is chemically bonded to M; and wherein each Cp ligand group is chemically bonded to M.

The ligands represented by $Cp^A$ and $Cp^B$ in formula (I) may be the same or different cyclopentadienyl ligands or ligands isolobal to cyclopentadienyl, either or both of which may contain heteroatoms and/or may be substituted by a group R. Non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$Ind"), substituted versions thereof, and heterocyclic versions thereof. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ may be the same or different type of ligand that is bonded to M. In one embodiment of formula (I) only one of either $Cp^A$ or $Cp^B$ is present.

Independently, each $Cp^A$ and $Cp^B$ of formula (I) may be unsubstituted or substituted with any one or combination of substituent groups R. Non-limiting examples of substituent groups R as used in structure (I) as well as ring substituents in structures (VIa-d) include groups selected from hydrogen radical, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof.

More particular non-limiting examples of alkyl substituents R associated with formula (I) through (VIa-b) include methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from carbon, nitrogen, oxygen, phosphorous, silicon, germanium, aluminum, boron and combinations thereof. Also, a substituent R group such as 1-butanyl may form a bonding association to the element M.

The one or more X groups are any desirable leaving groups as defined above. The value for n is an integer from 0 to 4 in one embodiment, and 0, 1 or 2 in a more particular embodiment of formula (I). In one embodiment, two or more X's form a part of a fused ring or ring system.

In another aspect of the invention, the metallocene catalyst component includes those of formula (I) where $Cp^A$ and $Cp^B$ are bridged to each other by at least one bridging group, A, such that the structure is represented by formula (II):

$$Cp^A(A)Cp^B MX_n \quad (II)$$

These bridged compounds represented by formula (II) are known as "bridged metallocenes". $Cp^A$, $Cp^B$, M, X and n in structure (II) are as defined above; and wherein each Cp ligand is chemically bonded to M, and A is chemically bonded to each Cp. Non-limiting examples of bridging group A include hydrocarbon groups containing at least one Group 13 to 16 atom, such as but not limited to at least one of a carbon, oxygen, nitrogen, silicon, aluminum, boron, germanium and tin atom and combinations thereof. The bridging group A may also contain substituent groups R as defined above (for formula (I)) including halogen radicals and iron. More particular non-limiting examples of bridging group A are represented by $C_1$ to $C_6$ alkylenes, substituted $C_1$ to $C_6$ alkylenes, oxygen, sulfur, R'$_2$C=, R'$_2$Si=, —Si(R')$_2$Si(R')$_2$—, R'$_2$Ge=, R'P=(wherein-"="- represents two chemical bonds), where R' is independently selected from hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (II) has two or more bridging groups A.

Other non-limiting examples of bridging group A include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group A may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are divalent groups such as cyclobutylene, cyclopentylene, cyclohexylene, cycloheptylene, cyclooctylene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups A may be saturated or unsaturated and/or carry one or more substituents and/or be fused to one or more other ring structures. If present, the one or more substituents are preferably selected from hydrocarbyl (e.g., alkyl such as methyl) and halogen (e.g., F, Cl). The one or more Cp groups which the above cyclic bridging moieties may optionally be fused to may be saturated or unsaturated and are selected from those having 4 to 10, more particularly 5, 6 or 7 ring members (selected from C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formulae (I) and (II) are different from each other in one embodiment, and the same in another embodiment.

In yet another aspect of the invention, the metallocene catalyst components include bridged mono-ligand metallocene compounds (e.g., mono cyclopentadienyl catalyst components). In this embodiment, the at least one metallocene catalyst component is a bridged "half-sandwich" metallocene represented by the formula (III):

$$Cp^A(A)QMX_n \qquad (III)$$

wherein $Cp^A$ group represented in formula (III) is a substituted or unsubstituted ligand bonded to M as defined in (I) for Cp groups; a atom from the Q group is bonded to M; and A is a bridging group bonded to Q and $Cp^A$; and n is an integer 0, 1 or 2. In formula (III) above, $Cp^A$, A and Q may form a fused ring system. The X groups and n of formula (III) are as defined above. In one embodiment, $Cp^A$ is selected from the group consisting of cyclopentadienyl, indenyl, tetrahydroindenyl, fluorenyl, substituted versions thereof, and combinations thereof.

In formula (III), Q is a heteroatom-containing ligand in which the bonding atom (the atom that is bonded with the metal M) is selected from Group 15 atoms and Group 16 atoms in one embodiment, and selected from nitrogen, phosphorus, oxygen or sulfur atom in a more particular embodiment, and nitrogen and oxygen in yet a more particular embodiment. Non-limiting examples of Q groups include alkylamines, arylamines, mercapto compounds, ethoxy compounds, carboxylates (e.g., pivalate), carbamates, and other compounds comprising Group 15 and Group 16 atoms capable of bonding with M.

In yet another aspect of the invention, the at least one metallocene catalyst component is an unbridged "half sandwich" metallocene represented by the formula (IVa):

$$Cp^A MQ_q X_n \qquad (IVa)$$

wherein $Cp^A$ is defined as for the Cp groups in (I) and is a ligand that is bonded to M; each Q is independently bonded to M; X is a leaving group as described above; n ranges from 0 to 3, and is 0 or 3 in one embodiment; q ranges from 0 to 3, and is 0 or 3 in one embodiment. In one embodiment, $Cp^A$ is selected from the group consisting of cyclopentadienyl, indenyl, tetrahydroindenyl, fluorenyl, substituted version thereof, and combinations thereof.

In formula (IVa), Q is selected from ROO⁻, RO⁻, R(O)—, —NR—, —CR₂—, —S—, —NR₂, —CR₃, —SR, —SiR₃, —PR₂, —H, and substituted and unsubstituted aryl groups, wherein R is selected from $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ allyls, and $C_2$ to $C_{20}$ heteroallyl moieties.

Described another way, the "half sandwich" metallocenes above can be described as in formula (IVb), such as described in, for example, U.S. Pat. No. 6,069,213:

$$Cp^A M(Q_2 GZ)X_n \text{ or} \qquad (IVb)$$
$$T(Cp^A M(Q_2 GZ)X_n)_m$$

wherein M, $Cp^A$, X and n are as defined above;
$Q_2GZ$ forms a polydentate ligand unit (e.g., pivalate), wherein the Q groups form a bond with M, and is defined such that each Q is independently selected from —O—, —NR—, —CR₂— and —S—; G is either carbon or sulfur; and Z is selected from —OR, —NR₂, —CR₃, —SR, —SiR₃, —PR₂, and hydride, providing that when Q is —NR—, then Z is selected from —OR, —NR₂, —SR, —SiR₃, —PR₂; wherein each R is independently selected from $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;
n is 1 or 2 in a particular embodiment;
T is a bridging group selected from $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^A M(Q_2 GZ)X_n$" groups, and is chemically bonded to the $Cp^A$ groups;
m is an integer from 1 to 7; m is an integer from 2 to 6 in a more particular embodiment.

In yet another aspect of the invention, the at least one metallocene catalyst component is a bridged heterocyclic ligand complex represented by the formula (V):

$$((ZD)A_t(YB))_q MX_n \qquad (V)$$

wherein M is defined above; YB and ZD are groups isolobal to cyclopentadienyl and each bonded to M; each X is, if present, defined above;
one or more of B and D are heteroatoms selected from Group 13 to Group 16 elements in one embodiment; and selected from nitrogen, oxygen, sulfur, phosphorus and boron in a more particular embodiment; B and D may be the same or different
Y comprises B, wherein Y is a cyclic group comprising from 2 to 40 non-hydrogen atoms, from 2 to 20 carbon atoms in one embodiment; wherein YB may be substituted;
Z comprises D, where Z is a cyclic group comprising from 2 to 40 non-hydrogen atoms, from 2 to 20 carbon atoms in one embodiment; wherein ZD may be substituted;
t is 0 or 1; when t is 1, A, as defined in formula (II), is a bridging group joined to at least one of ZD or YB in one embodiment; and
q is 1 or 2; n is an integer from 0 to 4; all other groups in formula (V) are as defined above in (I) and (II).

In one embodiment, ZD and YB of formula (V) are selected from oxygen, sulfur, phosphorous and nitrogen heterocyclic derivatives of cyclopentadienyl, indenyl, tetrahydroindenyl, fluorenyl, substituted derivatives of each, and combinations thereof.

In another aspect of the invention, the at least one metallocene catalyst component can be described more particularly as embodiments of the formulae (I)–(V), as shown below in structures (VIa), (VIb), (VIc) and (VId):

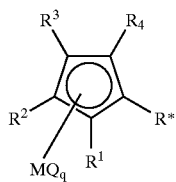

(VIa-i)

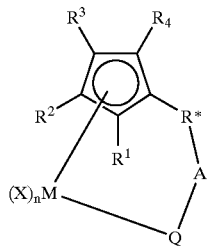

(VIa-ii)

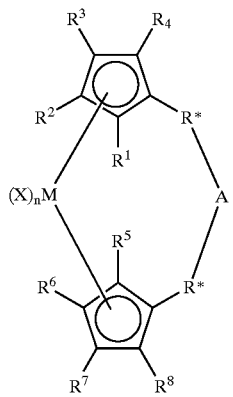

(VIb)

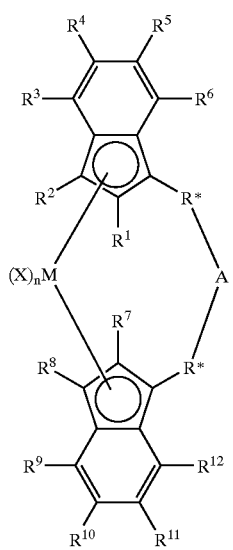

(VIc)

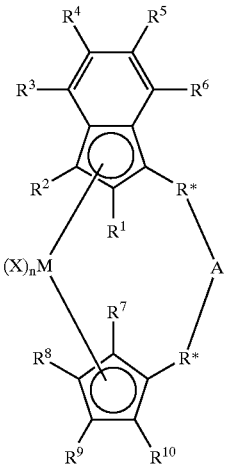

(VId)

wherein M is as described above;

Q in (VIa–i) and (VIa–ii) is selected from halogen ions, alkyls, alkylenes, aryls, arylenes, alkoxys, aryloxys, amines, alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, dimethylacetate, methylacetate, p-toluate, benzoate, diethylcarbamate, and dimethylcarbamate), fluorinated alkyls, fluorinated aryls, and fluorinated alkylcarboxylates;

q is an integer ranging from 1 to 3;

wherein each R* is independently: selected from hydrocarbyls and heteroatom-containing hydrocarbyls in one embodiment; and selected from alkylenes, substituted alkylenes and heteroatom-containing hydrocarbyls in another embodiment; selected from $C_1$ to $C_{12}$ alkylenes, $C_1$ to $C_{12}$ substituted alkylenes, and $C_1$ to $C_{12}$ heteroatom-containing hydrocarbons in a more particular embodiment; and selected from $C_1$ to $C_4$ alkylenes in yet a more particular embodiment; and wherein both R* groups are identical in another embodiment of structures (VIb–d);

A is as described above for structure (II), and more particularly, selected from —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from $C_5$ to $C_8$ cyclic hydrocarbons, —CH$_2$CH$_2$—, =CR$_2$ and =SiR$_2$ in a more particular embodiment; wherein and R is selected from alkyls, cycloalkyls, aryls, alkoxys, fluoroalkyls and heteroatom-containing hydrocarbons in one embodiment; and R is selected from $C_1$ to $C_6$ alkyls, substituted phenyls, phenyl, and $C_1$ to $C_6$ alkoxys in a more particular embodiment; and R is selected from methoxy, methyl, phenoxy, and phenyl in yet a more particular embodiment;

wherein A may be absent in yet another embodiment, in which case each R* is defined as for $R^1$–$R^{10}$;

each X is independently selected from any leaving group as defined above;

n is an integer from 0 to 4, and from 1 to 3 in another embodiment, and from 1 to 2 in yet another embodiment; and $R^1$ through $R^{10}$ are independently: selected from hydrogen radical, halogen radicals, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and selected from hydrogen radical, fluorine radical, chlorine radical, methyl, ethyl, propyl, isopropyl, butyl, isobutyl, tertiary butyl, hexyl, phenyl, 2,6-di-methylphenyl, and 4-tertiarybutylphenyl groups in yet a more particular embodiment; wherein adjacent R groups may form a ring, either saturated, partially saturated, or completely saturated.

The structure of the metallocene catalyst component represented by (VIa–i) and (VIa–ii) may take on many forms such as disclosed in, for example, U.S. Pat. Nos. 6,248,912, 5,026,798, 5,703,187, and 5,747,406, including a dimer or oligomeric structure, such as disclosed in, for example, U.S. Pat. Nos. 5,026,798 and 6,069,213.

In a particular embodiment of the metallocene represented in (VId), $R^1$ and $R^2$ form a conjugated 6-membered carbon ring system (thus forming a fluorenyl) that may or may not be substituted.

Non-limiting examples of metallocene catalyst components consistent with the description herein include:

(cyclopentadienyl)zirconium $X_n$,
(indenyl)zirconium $X_n$,
(1-methylindenyl)zirconium $X_n$,
(2-methylindenyl)zirconium $X_n$,
(1-propylindenyl)zirconium $X_n$,
(2-propylindenyl)zirconium $X_n$,
(1-butylindenyl)zirconium $X_n$,
(2-butylindenyl)zirconium $X_n$,
(methylcyclopentadienyl)zirconium $X_n$,
(tetrahydroindenyl)zirconium $X_n$,
(pentamethylcyclopentadienyl)zirconium $X_n$,
(cyclopentadienyl)zirconium $X_n$,
pentamethylcyclopentadienyltitanium $X_n$,
tetramethylcyclopentadienyltitanium $X_n$,
1,2,4-trimethylcyclopentadienylzirconium $X_n$,
dimethylsilyl(1,2,3,4-tetramethylcyclopentadienyl)(cyclopentadienyl)zirconium $X_n$,
dimethylsilyl(1,2,3,4-tetramethylcyclopentadienyl)(1,2,3-trimethylcyclopentadienyl)zirconium $X_n$,
dimethylsilyl(1,2,3,4-tetramethylcyclopentadienyl)(1,2-dimethylcyclopentadienyl)zirconium $X_n$,
dimethylsilyl(1,2,3,4-tetramethyl-cyclopentadienyl)(2-methylcyclopentadienyl)zirconium $X_n$,
dimethylsilyl(cyclopentadienyl)(indenyl)zirconium $X_n$,
dimethylsilyl(2-methylindenyl)(fluorenyl)zirconium $X_n$,
diphenylsilyl(1,2,3,4-tetramethyl-cyclopentadienyl)(3-propylcyclopentadienyl)zirconium $X_n$,
dimethylsilyl(1,2,3,4-tetramethylcyclopentadienyl)(3-t-butylcyclopentadienyl)zirconium $X_n$,
dimethylgermyl(1,2-dimethylcyclopentadienyl)(3-isopropylcyclopentadienyl)zirconium $X_n$,
dimethylsilyl(1,2,3,4-tetramethyl-cyclopentadienyl)(3-methylcyclopentadienyl)zirconium $X_n$,
diphenylmethylidene(cyclopentadienyl)(9-fluorenyl)zirconium $X_n$,
diphenylmethylidene(cyclopentadienyl)(indenyl)zirconium $X_n$,
iso-propylidenebis(cyclopentadienyl)zirconium $X_n$,
iso-propylidene(cyclopentadienyl)(9-fluorenyl)zirconium $X_n$,
iso-propylidene(3-methylcyclopentadienyl)(9-fluorenyl)zirconium $X_n$,
ethylenebis(9-fluorenyl)zirconium $X_n$,
meso-ethylenebis(1-indenyl)zirconium $X_n$,
ethylenebis(1-indenyl)zirconium $X_n$,
ethylenebis(2-methyl-1-indenyl)zirconium $X_n$,
ethylenebis(2-methyl-4,5,6,7-tetrahydro-1-indenyl)zirconium $X_n$,
ethylenebis(2-propyl-4,5,6,7-tetrahydro-1-indenyl)zirconium $X_n$,
ethylenebis(2-isopropyl-4,5,6,7-tetrahydro-1-indenyl)zirconium $X_n$,
ethylenebis(2-butyl-4,5,6,7-tetrahydro-1-indenyl)zirconium $X_n$,
ethylenebis(2-isobutyl-4,5,6,7-tetrahydro-1-indenyl)zirconium $X_n$,
dimethylsilyl(4,5,6,7-tetrahydro-1-indenyl)zirconium $X_n$,
diphenyl(4,5,6,7-tetrahydro-1-indenyl)zirconium $X_n$,
ethylenebis(4,5,6,7-tetrahydro-1-indenyl)zirconium $X_n$,
dimethylsilylbis(cyclopentadienyl)zirconium $X_n$,
dimethylsilylbis(9-fluorenyl)zirconium $X_n$,
dimethylsilylbis(1-indenyl)zirconium $X_n$,
dimethylsilylbis(2-methylindenyl)zirconium $X_n$,
dimethylsilylbis(2-propylindenyl)zirconium $X_n$,
dimethylsilylbis(2-butylindenyl)zirconium $X_n$,
diphenylsilylbis(2-methylindenyl)zirconium $X_n$,
diphenylsilylbis(2-propylindenyl)zirconium $X_n$,
diphenylsilylbis(2-butylindenyl)zirconium $X_n$,
dimethylgermylbis(2-methylindenyl)zirconium $X_n$
dimethylsilylbis(tetrahydroindenyl)zirconium $X_n$,
dimethylsilylbis(tetramethylcyclopentadienyl)zirconium $X_n$,
dimethylsilyl(cyclopentadienyl)(9-fluorenyl)zirconium $X_n$,
diphenylsilyl(cyclopentadienyl)(9-fluorenyl)zirconium $X_n$,
diphenylsilylbis(indenyl)zirconium $X_n$,
cyclotrimethylenesilyl(tetramethylcyclopentadienyl)(cyclopentadienyl)zirconium $X_n$,
cyclotetramethylenesilyl(tetramethylcyclopentadienyl)(cyclopentadienyl)zirconium $X_n$,
cyclotrimethylenesilyl(tetramethylcyclopentadienyl)(2-methylindenyl)zirconium $X_n$,
cyclotrimethylenesilyl(tetramethylcyclopentadienyl)(3methylcyclopentadienyl)zirconium $X_n$,
cyclotrimethylenesilylbis(2-methylindenyl)zirconium $X_n$,
cyclotrimethylenesilyl(tetramethylcyclopentadienyl)(2,3,5-trimethylcyclopentadienyl)zirconium $X_n$,
cyclotrimethylenesilylbis(tetramethylcyclopentadienyl)zirconium $X_n$,
dimethylsilyl(tetramethylcyclopentadienyl)(N-tert-butylamido)titanium $X_n$,
bis(cyclopentadienyl)zirconium $X_n$,
bis(n-butylcyclopentadienyl)zirconium $X_n$,
bis(n-dodecylcyclopentadienyl)zirconium $X_n$,
bis(ethylcyclopentadienyl)zirconium $X_n$,
bis(iso-butylcyclopentadienyl)zirconium $X_n$,
bis(iso-propylcyclopentadienyl)zirconium $X_n$,
bis(methylcyclopentadienyl)zirconium $X_n$,
bis(n-octylcyclopentadienyl)zirconium $X_n$,
bis(n-pentylcyclopentadienyl)zirconium $X_n$,
bis(n-propylcyclopentadienyl)zirconium $X_n$,
bis(trimethylsilylcyclopentadienyl)zirconium $X_n$,
bis(1,3-bis(trimethylsilyl)cyclopentadienyl)zirconium $X_n$,
bis(1-ethyl-2-methylcyclopentadienyl)zirconium $X_n$,
bis(1-ethyl-3-methylcyclopentadienyl)zirconium $X_n$, bis(pentamethylcyclopentadienyl)zirconium $X_n$,
bis(1-propyl-3-methylcyclopentadienyl)zirconium $X_n$,
bis(1-n-butyl-3-methylcyclopentadienyl)zirconium $X_n$,
bis(1-isobutyl-3-methylcyclopentadienyl)zirconium $X_n$,
bis(1-propyl-3-butylcyclopentadienyl)zirconium $X_n$,
bis(1,3-di-n-butylcyclopentadienyl)zirconium $X_n$,
bis(4,7-dimethylindenyl)zirconium $X_n$,
bis(indenyl)zirconium $X_n$,
bis(2-methylindenyl)zirconium $X_n$,
cyclopentadienylindenylzirconium $X_n$,
bis(n-propylcyclopentadienyl)hafnium $X_n$,
bis(n-butylcyclopentadienyl)hafnium $X_n$,
bis(n-pentylcyclopentadienyl)hafnium $X_1$,
(n-propyl cyclopentadienyl)(n-butyl cyclopentadienyl) hafnium $X_n$,
bis[(2-trimethylsilylethyl)cyclopentadienyl]hafnium $X_n$,
bis(trimethylsilyl cyclopentadienyl)hafnium $X_n$,
bis(2-n-propylindenyl)hafnium $X_n$,
bis(2-n-butylindenyl)hafnium $X_n$,
dimethylsilylbis(n-propylcyclopentadienyl)hafnium $X_n$,
dimethylsilylbis(n-butylcyclopentadienyl)hafnium $X_n$,
bis(9-n-propylfluorenyl)hafnium $X_n$,
bis(9-n-butylfluorenyl)hafnium $X_n$,
(9-n-propylfluorenyl)(2-n-propylindenyl)hafnium $X_n$,
bis(1-n-propyl-2-methylcyclopentadienyl)hafnium $X_n$,
(n-propylcyclopentadienyl)(1-n-propyl-3-n-butylcyclopentadienyl)hafnium $X_n$,
dimethylsilyl(tetramethylcyclopentadienyl)(cyclopropylamido)titanium $X_n$,
dimethylsilyl(tetramethylcyclopentadienyl)(cyclobutylamido)titanium $X_n$,
dimethylsilyl(tetramethylcyclopentadienyl)(cyclopentylamido)titanium $X_n$,
dimethylsilyl(tetramethylcyclopentadienyl)(cyclohexylamido)titanium $X_n$,
dimethylsilyl(tetramethylcyclopentadienyl)(cycloheptylamido)titanium $X_n$,
dimethylsilyl(tetramethylcyclopentadienyl)(cyclooctylamido)titanium $X_n$,
dimethylsilyl(tetramethylcyclopentadienyl)(cyclononylamido)titanium $X_n$,
dimethylsilyl(tetramethylcyclopentadienyl)(cyclodecylamido)titanium $X_n$,
dimethylsilyl(tetramethylcyclopentadienyl)(cycloundecylamido)titanium $X_n$,
dimethylsilyl(tetramethylcyclopentadienyl)(cyclododecylamido)titanium $X_n$,
dimethylsilyl(tetramethylcyclopentadienyl)(sec-butylamido)titanium $X_n$,
dimethylsilyl(tetramethylcyclopentadienyl)(n-octylamido)titanium $X_n$,
dimethylsilyl(tetramethylcyclopentadienyl)(n-decylamido)titanium $X_n$,
dimethylsilyl(tetramethylcyclopentadienyl)(n-octadecylamido)titanium $X_n$,
methylphenylsilyl(tetramethylcyclopentadienyl)(cyclopropylamido)titanium $X_n$,
methylphenylsilyl(tetramethylcyclopentadienyl)(cyclobutylamido)titanium $X_n$,
methylphenylsilyl(tetramethylcyclopentadienyl)(cyclopentylamido)titanium $X_n$,
methylphenylsilyl(tetramethylcyclopentadienyl)(cyclohexylamido)titanium $X_n$,
methylphenylsilyl(tetramethylcyclopentadienyl)(cycloheptylamido)titanium $X_n$,
methylphenylsilyl(tetramethylcyclopentadienyl)(cyclooctylamido)titanium $X_n$,
methylphenylsilyl(tetramethylcyclopentadienyl)(cyclononylamido)titanium $X_n$,
methylphenylsilyl(tetramethylcyclopentadienyl)(cyclodecylamido)titanium $X_n$,
methylphenylsilyl(tetramethylcyclopentadienyl)(cycloundecylamido)titanium $X_n$,
methylphenylsilyl(tetramethylcyclopentadienyl)(cyclododecylamido)titanium $X_n$,
methylphenylsilyl(tetramethylcyclopentadienyl)(sec-butylamido)titanium $X_n$,
methylphenylsilyl(tetramethylcyclopentadienyl)(n-octylamido)titanium $X_n$,
methylphenylsilyl(tetramethylcyclopentadienyl)(n-decylamido)titanium $X_n$,
methylphenylsilyl(tetramethylcyclopentadienyl)(n-octadecylamido)titanium $X_n$,
diphenylsilyl(tetramethylcyclopentadienyl)(cyclopropylamido)titanium $X_n$,
diphenylsilyl(tetramethylcyclopentadienyl)(cyclobutylamido)titanium $X_n$,
diphenylsilyl(tetramethylcyclopentadienyl)(cyclopentylamido)titanium $X_n$,
diphenylsilyl(tetramethylcyclopentadienyl)(cyclohexylamido)titanium $X_n$,
diphenylsilyl(tetramethylcyclopentadienyl)(cycloheptylamido)titanium $X_n$,
diphenylsilyl(tetramethylcyclopentadienyl)(cyclooctylamido)titanium $X_n$,
diphenylsilyl(tetramethylcyclopentadienyl)(cyclononylamido)titanium $X_n$,
diphenylsilyl(tetramethylcyclopentadienyl)(cyclodecylamido)titanium $X_n$,
diphenylsilyl(tetramethylcyclopentadienyl)(cycloundecylamido)titanium $X_n$,
diphenylsilyl(tetramethylcyclopentadienyl)(cyclododecylamido)titanium $X_n$,
diphenylsilyl(tetramethylcyclopentadienyl)(sec-butylamido)titanium $X_n$,
diphenylsilyl(tetramethylcyclopentadienyl)(n-octylamido) titanium $X_n$,
diphenylsilyl(tetramethylcyclopentadienyl)(n-decylamido) titanium $X_n$,
diphenylsilyl(tetramethylcyclopentadienyl)(n-octadecylamido)titanium $X_n$, and derivatives thereof, and mixtures thereof.

By "derivatives thereof", it is meant any substitution or ring formation as described above for structures (VIa–d) in one embodiment; and in particular, replacement of the metal (Zr, Ti or Hf) with an atom selected from Zr, Hf and Ti; and replacement of the "X" group with any other group as defined above.

More particularly, non-limiting examples of the fluorided catalyst components produced by the method of the invention are as follows:

Bis(methylcyclopentadienyl)zirconium difluoride,
Bis(ethylcyclopentadienyl)zirconium difluoride,
Bis(propylcyclopentadienyl)zirconium difluoride,
Bis(isopropylcyclopentadienyl)zirconium difluoride,
Bis(butylcyclopentadienyl)zirconium difluoride,
Bis(isobutylcyclopentadienyl)zirconium difluoride,
Bis(neopentylcyclopentadienyl)zirconium difluoride,
Bis(cyclopentylcyclopentadienyl)zirconium difluoride,
Bis(cyclohexylmethylcyclopentadienyl)zirconium difluoride,
Bis(allylcyclopentadienyl)zirconium difluoride, Bis((3-butenyl)cyclopentadienyl)zirconium difluoride,
Bis(trimethylsilylcyclopentadienyl)zirconium difluoride,
Bis(trimethylgermylcyclopentadienyl)zirconium difluoride,
Bis(trimethylsilylmethylcyclopentadienyl)zirconium difluoride,
Bis(1,2-dimethylcyclopentadienyl)zirconium difluoride,
Bis(1,3-dimethylcyclopentadienyl)zirconium difluoride,
Bis(1,2,3-trimethylcyclopentadienyl)zirconium difluoride,
Bis(1,2,4-trimethylcyclopentadienyl)zirconium difluoride,
Bis(tetramethylcyclopentadienyl)zirconium difluoride,
Bis(1,3-methylethylcyclopentadienyl)zirconium difluoride,
Bis(1,3-methylpropylcyclopentadienyl)zirconium difluoride,
Bis(1,3-methylbutylcyclopentadienyl)zirconium difluoride,
Bis(phenylcyclopentadienyl)zirconium difluoride,
Bis(1,3-methylphenylcyclopentadienyl)zirconium difluoride,
Bis(benzylcyclopentadienyl)zirconium difluoride,
Bis(1,3-methylbenzylcyclopentadienyl)zirconium difluoride,
Bis(phenethylcyclopentadienyl)zirconium difluoride,
Bis((3-phenylpropyl)cyclopentadienyl)zirconium difluoride,
(Tetramethylcylopentadienyl)(propylcyclopentadienyl)zirconium difluoride,
(Pentamethylcylopentadienyl)(propylcyclopentadienyl)zirconium difluoride,
Cyclopentadienyl(propylcyclopentadienyl)zirconium difluoride,
Cyclopentadienyl(butylcyclopentadienyl)zirconium difluoride,
Cyclopentadienyl(cyclopentylcyclopentadienyl)zirconium difluoride,
Cyclopentadienyl (tetrahydroindenyl)zirconium difluoride,
Cyclopentadienyl(1,3-methylbutylcyclopentadienyl)zirconium difluoride,
Cyclopentadienyl(tetramethylcyclopentadienyl)zirconium difluoride,
Cyclopentadienyl(propyltetramethylcyclopentadienyl)zirconium difluoride,
Cyclopentadienyl(butyltetramethylcyclopentadienyl)zirconium difluoride,
Cyclopentadienyl(cyclopentyltetramethylcyclopentadienyl)zirconium difluoride,
Cyclopentadienyl(indenyl)zirconium difluoride,
Cyclopentadienyl(1-methylindenyl)zirconium difluoride,
Cyclopentadienyl(fluorenyl)zirconium difluoride,
Cyclopentadienyl(tetrahydrofluorenyl)zirconium difluoride,
Cyclopentadienyl(octahydrofluorenyl)zirconium difluoride,
Bis(tetrahydroindenyl)zirconium difluoride,
Bis(trihydropentalenyl)zirconium difluoride,
Bis(pentahydroazulenyl)zirconium difluoride,
Dimethylsilylbis(tetrahydroindenyl)zirconium difluoride,
Ethylenebis(tetrahydroindenyl)zirconium difluoride,
Bis(indenyl)zirconium difluoride,
Bis(1-methylindenyl)zirconium difluoride,
Bis(2-methylindenyl)zirconium difluoride,
Bis(4,7-dimethylindenyl)zirconium difluoride,
Bis(5,6-dimethylindenyl)zirconium difluoride,
Bis(1-phenylindenyl)zirconium difluoride,
Bis(2-phenylindenyl)zirconium difluoride,
Bis(fluorenyl)zirconium difluoride,
Bis(1-methylfluorenyl)zirconium difluoride,
Bis(2,7-di-t-butylfluorenyl)zirconium difluoride,
Dimethylsilylbis(3-methylcyclopentadienyl)zirconium difluoride,
Dimethylsilylbis(3-propylcyclopentadienyl)zirconium difluoride,
Dimethylsilylbis(2,4-dimethylcyclopentadienyl)zirconium difluoride,
Dimethylsilylbis(2,3,5-trimethylcyclopentadienyl)zirconium difluoride,
Dimethylsilylbis(tetramethylcyclopentadienyl)zirconium difluoride,
Dimethylsilylbis(indenyl)zirconium difluoride,
Dimethylsilylbis(2-methylindenyl)zirconium difluoride,
Dimethylsilylbis(2-methyl-4-phenylindenyl)zirconium difluoride,
Dimethylsilylbis(2-methyl-4-(3,5-di-t-butyl)phenylindenyl)zirconium difluoride,
Dimethylsilylbis(2-methyl-4-naphthylindenyl)zirconium difluoride,
Dimethylsilyl(cyclopentadienyl)(indenyl)zirconium difluoride,
Dimethylsilyl(tetramethylcyclopentadienyl)(indenyl)zirconium difluoride,
Silacyclobutyl(tetramethylcyclopentadienyl)(indenyl)zirconium difluoride,
Silacyclopentyl(tetramethylcyclopentadienyl)(indenyl)zirconium difluoride,
Ethylenebis(indenyl)zirconium difluoride,
Ethylenebis(2-methylindenyl)zirconium difluoride,
Isopropylidene(cyclopentadienyl)(fluorenyl)zirconium difluoride,
Diphenylmethylidene(cyclopentadienyl)(fluorenyl)zirconium difluoride,
Dimethylsilyl(cyclopentadienyl)(fluorenyl)zirconium difluoride,
Diphenylsilyl(cyclopentadienyl)(fluorenyl)zirconium difluoride,
Dimethylsilylbis(fluorenyl)zirconium difluoride,
Ethylenebis(fluorenyl)zirconium difluoride,
Bis(methylcyclopentadienyl)hafnium difluoride,
Bis(ethylcyclopentadienyl)hafnium difluoride,
Bis(propylcyclopentadienyl)hafnium difluoride,
Bis(butylcyclopentadienyl)hafnium difluoride,
Bis(isobutylcyclopentadienyl)hafnium difluoride,
Bis(neopentylcyclopentadienyl)hafnium difluoride,
Bis(cyclopentylcyclopentadienyl)hafnium difluoride,
Bis(allylcyclopentadienyl)hafnium difluoride,
Bis((3-butenyl)cyclopentadienyl)hafnium difluoride,
Bis(cyclohexylmethylcyclopentadienyl)hafnium difluoride,
Bis(trimethylsilylmethylcyclopentadienyl)hafnium difluoride,
Bis((3-phenylpropyl)cyclopentadienyl)hafnium difluoride,
Bis(1,3-methylbutylcyclopentadienyl)hafnium difluoride,
Bis(1,3-methylpropylcyclopentadienyl)hafnium difluoride,
Ethylenebis(indenyl)hafnium difluoride,
Dimethylsilylbis(3-propylcyclopentadienyl)hafnium difluoride,
Dimethylsilylbis(2,4-methylpropylcyclopentadienyl)hafnium difluoride,
Dimethylsilylbis(tetramethylcyclopentadienyl)hafnium difluoride,
Dimethylsilylbis(indenyl)hafnium difluoride,
Diphenylsilylbis(indenyl)hafnium difluoride,
Bis(cyclopentadienyl)titanium difluoride,
Bis(methylcyclopentadienyl)titanium difluoride,
Bis(ethylcyclopentadienyl)titanium difluoride,
Bis(propylcyclopentadienyl)titanium difluoride,
Bis(butylcyclopentadienyl)titanium difluoride,
Bis(isobutylcyclopentadienyl)titanium difluoride,
Bis(neopentylcyclopentadienyl)titanium difluoride,
Bis(cyclopentylcyclopentadienyl)titanium difluoride,
Ethylenebis(indenyl)titanium difluoride, Dimethylsilylbis(indenyl)titanium difluoride,
Diphenylsilyl(cyclopentadienyl)(fluorenyl)titanium difluoride,
(cyclopentadienyl)zirconium trifluoride,
(indenyl)zirconium trifluoride,
(1-methylindenyl)zirconium trifluoride,
(2-methylindenyl)zirconium trifluoride,
(1-propylindenyl)zirconium trifluoride,
(2-propylindenyl)zirconium trifluoride,
(1-butylindenyl)zirconium trifluoride,
(2-butylindenyl)zirconium trifluoride,
(methylcyclopentadienyl)zirconium trifluoride,
(tetrahydroindenyl)zirconium trifluoride,
(pentamethylcyclopentadienyl)zirconium trifluoride,
(cyclopentadienyl)zirconium trifluoride,
pentamethylcyclopentadienyltitanium trifluoride,
tetramethylcyclopentyldienyltitanium trifluoride,
1,2,4-trimethylcyclopentadienylzirconium trifluoride, and mixtures thereof.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" useful in the present invention may comprise any combination of any "embodiment" described herein.

Activator

An activator is present with the catalyst system comprising the fluorided metallocene catalyst components of the present invention. As used herein, the term "activator" is defined to be any compound or combination of compounds, supported or unsupported, which can activate a single-site catalyst compound (e.g., metallocenes), such as by creating a cationic species from the catalyst component. Typically, this involves the abstraction of at least one leaving group (X group in the formulas/structures above) from the metal center of the catalyst component. The catalyst components of the present invention are thus activated towards olefin polymerization using such activators. Embodiments of such activators include Lewis acids such as cyclic or oligomeric poly(hydrocarbylaluminum oxides) and so called non-coordinating ionic activators ("NCA") (alternately, "ionizing activators" or "stoichiometric activators"), or any other compound that can convert a neutral metallocene catalyst component to a metallocene cation that is active with respect to olefin polymerization.

More particularly, it is within the scope of this invention to use Lewis acids such as alumoxane (e.g., "MAO"), modified alumoxane (e.g., "TIBAO"), and alkylaluminum compounds as activators, and/or ionizing activators (neutral or ionic) such as tri (n-butyl)ammonium tetrakis (pentafluorophenyl)boron and/or a trisperfluorophenyl boron metalloid precursors to activate desirable metallocenes described herein. MAO and other aluminum-based activators are well known in the art. Ionizing activators are well known in the art and are described by, for example, Eugene You-Xian Chen & Tobin J. Marks, *Cocatalysts for Metal-Catalyzed Olefin Polymerization: Activators, Activation Processes, and Structure-Activity Relationships* 100(4) CHEMICAL REVIEWS 1391–1434 (2000). The activators may be associated with or bound to a support, either in association with the catalyst component (e.g., metallocene) or separate from the catalyst component, such as described by Gregory G. Hlatky, *Heterogeneous Single-Site Catalysts for Olefin Polymerization* 100(4) CHEMICAL REVIEWS 1347–1374 (2000).

Non-limiting examples of aluminum alkyl compounds which may be utilized as activators for the catalyst precursor compounds for use in the methods of the present invention include trimethylaluminum, triethylaluminum, triisobutylaluminum, tri-n-hexylaluminum, tri-n-octylaluminum and the like.

Examples of neutral ionizing activators include Group 13 tri-substituted compounds, in particular, tri-substituted boron, aluminum, tellurium, aluminum, gallium and indium compounds, and mixtures thereof The three substituent groups are each independently selected from alkyls, alkenyls, halogen, substituted alkyls, aryls, arylhalides, alkoxy and halides. In one embodiment, the three groups are independently selected from halogen, mono- or multicyclic (including halosubstituted) aryls, alkyls, and alkenyl compounds and mixtures thereof. In another embodiment, the three groups are selected from alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls), and combinations thereof. In yet another embodiment, the three groups are selected from alkyls having 1 to 4 carbon groups, phenyl, naphthyl and mixtures thereof. In yet another embodiment, the three groups are selected from highly halogenated alkyls having 1 to 4 carbon groups, highly halogenated phenyls, and highly halogenated naphthyls and mixtures thereof By "highly halogenated", it is meant that at least 50% of the hydrogens are replaced by a halogen group selected from fluorine, chlorine and bromine. In yet another embodiment, the neutral stoichiometric activator is a tri-substituted Group 13 compound comprising highly fluorided aryl groups, the groups being highly fluorided phenyl and highly fluorided naphthyl groups.

In another embodiment, the neutral tri-substituted Group 13 compounds are boron compounds such as trisperfluorophenylboron, trisperfluoronaphthylboron, tris(3,5-di(trifluoromethyl)phenyl)boron, tris(di-t-butylmethylsilyl)perfluorophenylboron, and other highly fluorinated trisarylboron compounds and combinations thereof, and their aluminum equivalents (e.g., trisperfluorophenylaluminum). Other suitable neutral ionizing activators are described in U.S. Pat. Nos. 6,399,532 B1, 6,268,445 B1, and in 19 ORGANOMETALLICS 3332–3337 (2000), and in 17 ORGANOMETALLICS 3996–4003 (1998).

Illustrative, not limiting examples of ionic ionizing activators include trialkyl-substituted ammonium salts such as triethylammonium tetra(phenyl)boron, tripropylammonium tetra(phenyl)boron, tri(n-butyl)ammonium tetra(phenyl) boron, trimethylammonium tetra(p-tolyl)boron, trimethylammonium tetra(o-tolyl)boron, tributylammonium tetra (pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tributylammonium tetra (pentafluorophenyl)boron, tri(n-butyl)ammonium tetra(o-tolyl)boron and the like; N,N-dialkyl anilinium salts such as N,N-dimethylanilinium tetra(phenyl)boron, N,N-diethylanilinium tetra(phenyl)boron, N,N-2,4,6-pentamethylanilinium tetra(phenyl)boron and the like; dialkyl ammonium salts such as di-(isopropyl)ammonium tetra(pentafluorophenyl)boron, dicyclohexylammonium tetra(phenyl)boron and the like; and triaryl phosphonium salts such as triphenylphosphonium tetra(phenyl)boron, tri (methylphenyl)phosphonium tetra(phenyl)boron, tri (dimethylphenyl)phosphonium tetra(phenyl)boron and the like, and their aluminum equivalents.

In yet another embodiment of the activator of the invention, an alkylaluminum can be used in conjunction with a heterocyclic compound. The ring of the heterocyclic compound may includes at least one nitrogen, oxygen, and/or sulfur atom, and includes at least one nitrogen atom in one embodiment. The heterocyclic compound includes 4 or more ring members in one embodiment, and 5 or more ring members in another embodiment.

The heterocyclic compound for use as an activator with an alkylaluminum may be unsubstituted or substituted with one or a combination of substituent groups. Examples of suitable substituents include halogen, alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or any combination thereof. The substituents groups may also be substituted with halogens, particularly fluorine or bromine, or heteroatoms or the like.

Non-limiting examples of hydrocarbon substituents include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluoroethyl, difluoroethyl, iodopropyl, bromohexyl or chlorobenzyl.

In one embodiment, the heterocyclic compound is unsubstituted. In another embodiment one or more positions on the heterocyclic compound are substituted with a halogen atom or a halogen atom containing group, for example a halogenated aryl group. In one embodiment the halogen is selected from chlorine, bromine and fluorine, and selected from fluorine and bromine in another embodiment, and the halogen is fluorine in yet another embodiment.

Non-limiting examples of heterocyclic compounds utilized in the activator of the invention include substituted and unsubstituted pyrroles, imidazoles, pyrazoles, pyrrolines, pyrrolidines, purines, carbazoles, and indoles, phenyl indoles, 2,5-dimethylpyrroles, 3-pentafluorophenylpyrrole, 4,5,6,7-tetrafluoroindole or 3,4-difluoropyrroles.

In one embodiment, the heterocyclic compound described above is combined with an alkyl aluminum or an alumoxane to yield an activator compound which, upon reaction with a catalyst component, for example a metallocene, produces an active polymerization catalyst. Non-limiting examples of alkylaluminums include trimethylaluminum, triethylaluminum, triisobutylaluminum, tri-n-hexylaluminum, tri-n-octylaluminum, tri-isooctylaluminum, triphenylaluminum, and combinations thereof.

Other activators include those described in WO 98/07515 such as tris(2,2',2''-nonafluorobiphenyl)fluoroaluminate. Combinations of activators are also contemplated by the invention, for example, alumoxanes and ionizing activators in combinations. Other activators include aluminum/boron complexes, perchlorates, periodates and iodates including their hydrates; lithium(2,2'-bisphenyl-ditrimethylsilicate). 4THF; silylium salts in combination with a non-coordinating compatible anion. Also, methods of activation such as using radiation, electro-chemical oxidation, and the like are also contemplated as activating methods for the purposes of rendering the neutral metallocene-type catalyst compound or precursor to a metallocene-type cation capable of polymerizing olefins. Other activators or methods for activating metallocene-type catalyst compounds are described in for example, U.S. Pat. Nos. 5,849,852, 5,859,653 and 5,869,723 and WO 98/32775.

In general, the activator and catalyst component(s) are combined in mole ratios of activator to catalyst component from 1000:1 to 0.1:1, and from 300:1 to 1:1 in another embodiment, and from 150:1 to 1:1 in yet another embodiment, and from 50:1 to 1:1 in yet another embodiment, and from 10:1 to 0.5:1 in yet another embodiment, and from 3:1 to 0.3:1 in yet another embodiment, wherein a desirable range may include any combination of any upper mole ratio limit with any lower mole ratio limit described herein. When the activator is a cyclic or oligomeric poly(hydrocarbylaluminum oxide) (e.g., "MAO"), the mole ratio of activator to catalyst component ranges from 2:1 to 100,000:1 in one embodiment, and from 10:1 to 10,000:1 in another embodiment, and from 50:1 to 2,000:1 in yet another embodiment. When the activator is a neutral or ionic ionizing activator (e.g., trisperfluorophenylaluminum, trisperfluorophenylboron, ammonium and carbyl salts of tetra(pentafluorophenyl) boron compounds) such as a boron alkyl and the ionic salt of a boron alkyl, the mole ratio of activator to catalyst component ranges from 0.5:1 to 10:1 in one embodiment, and from 1:1 to 5:1 in yet another embodiment.

Supports

A support may also be present as part of the catalyst system of the invention. Supports, methods of supporting, modifying, and activating supports for single-site catalyst such as metallocenes are discussed in, for example, 1 METALLOCENE-BASED POLYOLEFINS 173–218 (J. Scheirs & W. Kaminsky eds., John Wiley & Sons, Ltd. 2000). The terms "support" or "carrier", as used herein, are used interchangeably and refer to any support material, a porous support material in a particular embodiment, including inorganic or organic support materials. Non-limiting examples of support materials include inorganic oxides and inorganic chlorides, and in particular such materials as talc, clay, silica, alumina, magnesia, zirconia, iron oxides, boria, calcium oxide, zinc oxide, barium oxide, thoria, aluminum phosphate gel, and polymers such as polyvinylchloride, non-functionalized polystyrene and substituted polystyrene, functionalized or crosslinked organic supports such as polystyrene divinyl benzene polyolefins or polymeric compounds, and mixtures thereof, and graphite, in any of its various forms.

The support may be contacted with the other components of the catalyst system in any number of ways. In one embodiment, the support is contacted with the activator to form an association between the activator and support, or a "bound activator". In another embodiment, the catalyst component may be contacted with the support to form a "bound catalyst component". In yet another embodiment, the support may be contacted with the activator and catalyst component together, or with each partially in any order. The components may be contacted by any suitable means as in a solution, slurry, or solid form, or some combination thereof, and may be heated when contacted to from 25° C. to 250° C.

Desirable carriers are inorganic oxides that include Group 2, 3, 4, 5, 13 and 14 oxides and chlorides. Support materials include silica, alumina, silica-alumina, magnesium chloride, graphite, and mixtures thereof in one embodiment. Other useful supports include magnesia, titania, zirconia, montmorillonite (EP 0 511 665 B1), phyllosilicate, and the like. Also, combinations of these support materials may be used, for example, silica-chromium, silica-alumina, silica-titania and the like. Additional support materials may include those porous acrylic polymers described in EP 0 767 184 B1.

In one aspect of the support useful in the invention, the support possess a surface area in the range of from 10 to 700 m$^2$/g, pore volume in the range of from 0.1 to 4.0 cm$^3$/g and average particle size in the range of from 5 to 500 µm. In another embodiment, the surface area of the carrier is in the range of from 50 to 500 m$^2$/g, pore volume of from 0.5 to 3.5 cm$^3$/g and average particle size of from 10 to 200 µm. In yet another embodiment, the surface area of the carrier is in the range is from 100 to 400 m$^2$/g, pore volume from 0.8 to 3.0 cm$^3$/g and average particle size is from 5 to 100 µm. The average pore size of the carrier of the invention typically has pore size in the range of from 10 to 1000 Å, from 50 to 500 Å in another embodiment, and from 75 to 350 Å in yet another embodiment.

In one embodiment of the support, graphite is used as the support. The graphite is a powder in one embodiment. In another embodiment, the graphite is flake graphite. In another embodiment, the graphite and has a particle size of from 1 to 500 microns, from 1 to 400 microns in another embodiment, and from 1 to 200 in yet another embodiment, and from 1 to 100 microns in yet another embodiment.

The support, especially an inorganic support or graphite support, may be pretreated such as by a halogenation process or other suitable process that, for example, associates a chemical species with the support either through chemical bonding, ionic interactions, or other physical or chemical interaction. Examples of desirable chemical species include alkyls, alkylamines, mercapto compounds and halogens (F, Cl, Br). In one embodiment, the support is fluorided. The fluorine compounds suitable for providing fluorine for the support are desirably inorganic fluorine containing compounds. Such inorganic fluorine containing compounds may be any compound containing a fluorine atom as long as it does not contain a carbon atom. Particularly desirable are inorganic fluorine containing compounds selected from the group consisting of $NH_4BF_4$, $(NH_4)_2SiF_6$, $NH_4PF_6$, $NH_4F$, $(NH_4)_2TaF_7$, $NH_4NbF_4$, $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_5$, $BrF_5$, $IF_7$, $NF_3$, $HF$, $BF_3$, $NHF_2$ and $NH_4HF_2$.

A desirable method of treating the support with the fluorine compound is to dry mix the two components by simply blending at a concentration of from 0.01 to 10.0 millimole F/g of support in one embodiment, and in the range of from 0.05 to 6.0 millimole F/g of support in another embodiment, and in the range of from 0.1 to 3.0 millimole F/g of support in yet another embodiment. The fluorine compound can be dry mixed with the support either before or after charging to the vessel for dehydration or calcining the support. Accordingly, the fluorine concentration present on the support is in the range of from 0.2 to 5 wt % in one embodiment, and from 0.6 to 3.5 wt % of support in another embodiment.

Another method of treating the support with the fluorine compound is to dissolve the fluorine in a solvent, such as water, and then contact the support with the fluorine containing solution (at the concentration ranges described herein). When water is used and silica is the support, it is desirable to use a quantity of water that is less than the total pore volume of the support. Desirably, the support and, for example, fluorine compounds are contacted by any suitable means such as by dry mixing or slurry mixing at a temperature of from 100° C. to 1000° C. in one embodiment, and from 200° C. to 800° C. in another embodiment, and from 300° C. to 600° C. in yet another embodiment, the contacting in any case taking place for between two to eight hours.

Dehydration or calcining of the support may or may also be carried out. In one embodiment, the support is calcined prior to reaction with the fluorine or other support-modifying compound. In another embodiment, the support is calcined and used without further modification, or calcined, followed by contacting with one or more activators and/or catalyst components. Suitable calcining temperatures range from 100° C. to 1000° C. in one embodiment, and from 300° C. to 900° C. in a more particular embodiment, and from 400° C. to 850° C. in yet a more particular embodiment. Calcining may take place in the absence of oxygen and moisture by using, for example, an atmosphere of dry nitrogen.

It is within the scope of the present invention to co-contact (or "co-immobilize") more than one catalyst component with a support. Non-limiting examples of co-immobilization of catalyst components include two or more of the same or different metallocene catalyst components, one or more metallocene with a Ziegler-Natta type catalyst, one or more metallocene with a chromium or "Phillips" type catalyst, one or more metallocenes with a Group 15-containing catalyst (e.g., zirconium bis-amide compounds such as in U.S. Pat. No. 6,300,438 B1), and any of these combinations with one or more activators. More particularly, co-supported combinations include metallocene A/metallocene A; metallocene A/metallocene B; metallocene/Ziegler Natta; metallocene/Group 15-containing catalyst; metallocene/chromium catalyst; metallocene/Ziegler Natta/Group 15-containing catalyst; metallocene/chromium catalyst/ Group 15-containing catalyst, any of the these with an activator, and combinations thereof.

Further, the catalyst system of the present invention can include any combination of activators and catalyst components, either supported or not supported, in any number of ways. For example, the catalyst component may include any one or both of metallocenes and/or Group 15-containing catalysts components, and may include any combination of activators, any of which may be supported by any number of supports as described herein. Non-limiting examples of catalyst systems useful in the present invention include MN+NCA; MN:S+NCA; NCA:S+MN; MN:NCA:S; MN+AlA; MN:S+AlA; AlA:S+MN; MN:AlA:S; AlA:S+NCA+MN; NCA:S+MN+AlA; G15+ NCA; G15:S+NCA; NCA:S+G15; G15:NCA:S; G15+AlA; G15:S+AlA; AlA:S+G15; G15:AlA:S; AlA:S+NCA+G15; NCA:S+G15+AlA; MN+NCA+G15; MN:S+NCA+G15; NCA:S+MN+G15; MN:NCA:S+G15; MN+G15+AlA; MN:S+AlA+G15; AlA:S+MN+G15; MN:AlA:S+G15; AlA:S+NCA+MN+G15; NCA:S+MN+AlA+G15; MN+NCA; G15:MN:S+NCA; G15:NCA:S+MN; G15:MN:NCA:S; G15:MN:S+AlA; G15:AlA:S+MN; G15:MN:AlA:S; G15:AlA:S+NCA+MN; G15:NCA:S+ MN+AlA; wherein "MN" is metallocene component, "NCA" is a non-coordinating activator including ionic and neutral boron and aluminum based compounds as described above, "AlA" is an aluminum alkyl and/or alumoxane based activator, "G15" is a Group 15-containing catalyst component as described above, and "S" is a support; and wherein the use of ":" with "S" means that that those groups next to the colon are associated with ("supported by") the support as by pretreatment and other techniques known in the art, and the "+" sign means that the additional component is not directly bound to the support but present with the support and species bound to the support, such as present in a slurry, solution, gas phase, or another way, but is not meant to be limited to species that have no physico-chemical interaction with the support and/or supported species. Thus, for example, the embodiment "MN:NCA:S+G15" means that a metallocene and NCA activator are bound to a support, and present in, for example, a gas phase polymerization with a Group 15-containing catalyst component.

Polymerization Process

The catalyst system useful in catalyzing the production of polyolefins include at least one fluorided catalyst component as described herein, and at least one activator. The catalyst system described herein is suitable for use in any olefin prepolymerization and/or polymerization process over a wide range of temperatures and pressures and other conditions. Suitable polymerization processes include solution, gas phase, slurry phase and a high pressure process, or a combination thereof. A desirable process is a gas phase or slurry phase polymerization of one or more olefins at least one of which is ethylene or propylene.

The temperatures at which polymerization takes place may be in the range of from −60° C. to 280° C. in one embodiment, and from 50° C. to 200° C. in another embodiment, and the pressures employed may be in the range from 1 atmosphere to 500 atmospheres or higher.

In one embodiment, the process of this invention is directed toward a solution, high pressure, slurry or gas phase polymerization process of one or more olefin monomers having from 2 to 30 carbon atoms, from 2 to 12 carbon atoms in another embodiment, and from 2 to 8 carbon atoms in yet another embodiment. The invention is particularly well suited to the polymerization of two or more olefin monomers of ethylene, propylene, 1-butene, 1-pentene, 4-methyl-1-pentene, 1-hexene, 1-octene and 1-decene.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In a desirable embodiment of the process of the invention, a copolymer of ethylene derived units is produced in a gas phase process, the comonomer being an α-olefin having from 4 to 15 carbon atoms in one embodiment, and from 4 to 12 carbon atoms in another embodiment, and from 4 to 8 carbon atoms in yet another embodiment.

In another embodiment of the process of the invention, ethylene or propylene is polymerized with at least two different comonomers, optionally one of which may be a diene, to form a terpolymer.

In the production of polyethylene or polypropylene, comonomers may be present in the polymerization reactor. When present, the comonomer may be present at any level with the ethylene or propylene monomer that will achieve the desired weight percent incorporation of the comonomer into the finished resin. In one embodiment of polyethylene production, the comonomer is present with ethylene in a mole ratio range of from 0.0001 (comonomer:ethylene) to 50, and from 0.0001 to 5 in another embodiment, and from 0.0005 to 1.0 in yet another embodiment, and from 0.001 to 0.5 in yet another embodiment. Expressed in absolute terms, in making polyethylene, the amount of ethylene present in the polymerization reactor may range to up to 1000 atmospheres pressure in one embodiment, and up to 500 atmospheres pressure in another embodiment, and up to 200 atmospheres pressure in yet another embodiment, and up to 100 atmospheres in yet another embodiment, and up to 50 atmospheres in yet another embodiment.

Hydrogen gas is often used in olefin polymerization to control the final properties of the polyolefin, such as described in POLYPROPYLENE HANDBOOK 76–78 (Hanser Publishers, 1996). Using the catalyst system of the present invention, is known that increasing concentrations (partial pressures) of hydrogen increase the melt flow rate (MFR) and/or melt index (MI) of the polyolefin generated. The MFR or MI can thus be influenced by the hydrogen concentration. The amount of hydrogen in the polymerization can be expressed as a mole ratio relative to the total polymerizable monomer, for example, ethylene, or a blend of ethylene and hexane or propene. The amount of hydrogen used in the polymerization process of the present invention is an amount necessary to achieve the desired MFR or MI of the final polyolefin resin. In one embodiment, the mole ratio of hydrogen to total monomer ($H_2$:monomer) is in a range of from greater than 0.0001 in one embodiment, and from greater than 0.0005 in another embodiment, and from greater than 0.001 in yet another embodiment, and less than 10 in yet another embodiment, and less than 5 in yet another embodiment, and less than 3 in yet another embodiment, and less than 0.10 in yet another embodiment, wherein a desirable range may comprise any combination of any upper mole ratio limit with any lower mole ratio limit described herein. Expressed another way, the amount of hydrogen in the reactor at any time may range to up to 5000 ppm, and up to 4000 ppm in another embodiment, and up to 3000 ppm in yet another embodiment, and between 50 ppm and 5000 ppm in yet another embodiment, and between 500 ppm and 2000 ppm in another embodiment.

In another embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using any suitable bridged metallocene-type catalysts such as described in, for example, U.S. Pat. Nos. 6,143,686, 6,143,911, 5,296,434 and 5,278,264.

Typically in a gas phase polymerization process a continuous cycle is employed wherein one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer.

Further, it is common to use a staged reactor employing two or more reactors in series, wherein one reactor may produce, for example, a high molecular weight component and another reactor may produce a low molecular weight component. In one embodiment of the invention, the polyolefin is produced using a staged gas phase reactor. This and other commercial polymerization systems are described in, for example, 2 METALLOCENE-BASED POLYOLEFINS 366–378 (John Scheirs & W. Kaminsky, eds. John Wiley & Sons, Ltd.

2000). Gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421.

The one or more reactor pressures in a gas phase process (either single stage or two or more stages) may vary from 100 psig (690 kPa) to 500 psig (3448 kPa), and in the range of from 200 psig (1379 kPa) to 400 psig (2759 kPa) in another embodiment, and in the range of from 250 psig (1724 kPa) to 350 psig (2414 kPa) in yet another embodiment.

The one or more reactor temperatures in the gas phase process may vary from 30° C. to 120° C., and from 60° C. to 115° C. in another embodiment, and in the range of from 70° C. to 110° C. in yet another embodiment, and in the range of from 70° C. to 95° C. in yet another embodiment. For purposes of this patent specification and appended claims the terms "polymerization temperature" and "reactor temperature" are interchangeable.

The gas phase reactor employing the catalyst system described herein is capable of producing from 500 lbs of polymer per hour (227 Kg/hr) to 200,000 lbs/hr (90,900 Kg/hr), and greater than 1000 lbs/hr (455 Kg/hr) in another embodiment, and greater than 10,000 lbs/hr (4540 Kg/hr) in yet another embodiment, and greater than 25,000 lbs/hr (11,300 Kg/hr) in yet another embodiment, and greater than 35,000 lbs/hr (15,900 Kg/hr) in yet another embodiment, and greater than 50,000 lbs/hr (22,700 Kg/hr) in yet another embodiment, and from 65,000 lbs/hr (29,000 Kg/hr) to 100,000 lbs/hr (45,500 Kg/hr) in yet another embodiment.

A slurry polymerization process generally uses pressures in the range of from 1 to 50 atmospheres and even greater and temperatures in the range of 0° C. to 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, a branched alkane in one embodiment. The medium employed should be liquid under the conditions of polymerization and relatively inert. When a propane medium is used the process must be operated above the reaction diluent critical temperature and pressure. In one embodiment, a hexane or an isobutane medium is employed.

Another desirable polymerization technique of the invention is referred to as a particle form polymerization, or a slurry process where the temperature is kept below the temperature at which the polymer goes into solution. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484 and 2 METALLOCENE-BASED POLYOLEFINS 322–332 (2000).

The slurry reactor employing the catalyst system described herein is capable of producing greater than 2000 lbs of polymer per hour (907 Kg/hr), and greater than 5000 lbs/hr (2268 Kg/hr) in another embodiment, and greater than 10,000 lbs/hr (4540 Kg/hr) in yet another embodiment. In another embodiment, the slurry reactor used in the process of the invention produces greater than 15,000 lbs of polymer per hour (6804 Kg/hr), and from 25,000 lbs/hr (11,340 Kg/hr) to 100,000 lbs/hr (45,500 Kg/hr) in yet another embodiment.

In one embodiment of the process of the invention, the slurry or gas phase process is operated in the presence of a Cp ligand metallocene-type catalyst system of the invention and in the absence of, or essentially free of, any scavengers, such as triethylaluminum, trimethylaluminum, tri-isobutylaluminum and tri-n-hexylaluminum and diethyl aluminum chloride, dibutyl zinc and the like. By "essentially free", it is meant that these compounds are not deliberately added to the reactor or any reactor components, and if present, are present to less than 1 ppm in the reactor.

In another embodiment, one or all of the catalysts are combined with up to 10 wt % of a metal stearate, (e.g., an aluminum stearate or aluminum distearate) based upon the weight of the catalyst system (or its components), any support and the stearate. In an alternate embodiment, a solution of the metal stearate is fed into the reactor. In another embodiment, the metal stearate is mixed with the catalyst and fed into the reactor separately. These agents may be mixed with the catalyst or may be fed into the reactor in a solution or a slurry with or without the catalyst system or its components.

In another embodiment, the supported catalyst(s) are combined with the activators and are combined, such as by tumbling and other suitable means, with up to 2 wt % of an antistatic agent, such as a methoxylated amine, an example of which is Kemamine AS-990 (ICI Specialties, Bloomington Del.). Further, additives may be present such as carboxylate metal salts, as disclosed in U.S. Pat. No. 6,300,436.

The process of the invention can be used to make any number of polyolefins, in particular, polyethylene and polypropylene, either homopolymer, random copolymers, block copolymer, LLDPE, HDPE, LDPE, VLDPE, and variations of these.

One aspect of the present invention is a method of producing polyolefins comprising the steps of (a) contacting at least one fluoriding agent with one or more alkylated metallocene catalyst components to produce a fluorided metallocene catalyst component; wherein from less than 2.0 equivalents of fluoriding agent are contacted for every equivalent of alkylated catalyst component; followed by (b) contacting the fluorided metallocene catalyst component with at least one activator and olefins selected from $C_2$ to $C_{12}$ olefins under polymerization conditions to produce a polyolefin. The fluoriding step of (a) in the method of producing olefins can include any of the embodiments described above for the fluoriding step. The step (a) may precede step (b) by any amount of time that is advantageous to the production of the polyolefins. For example, the fluoriding step may take place in a reaction vessel, isolated, then transferred to the polymerization reactor by any suitable means over a period of hours to days. The fluorided metallocene may be isolated and then supported on, for example, silica, as described above, and the silica itself may optionally be pre-treated with modifying agents (e.g., fluorided), and/or pre-contacted with an activator such as MAO or a stoichiometric boron compound (e.g., trisperfluorophenylboron). The fluorided metallocene, either supported or not, may be kept as a solid or slurried/dissolved in, for example toluene, mineral oil, or some other non-coordinating diluent. The slurried fluorided metallocene may be transferred as such into the polymerization reactor. Given the relatively high activity of such catalysts, there is an advantage that low quantities of the fluorided metallocene are necessary to affect polymerization.

The methods of the present invention can be described alternately by any of the embodiments disclosed herein. The present invention, while not meant to be limiting by, may be better understood by reference to the following examples and Tables.

EXAMPLES

The examples below were obtained as described. The fluorided metallocene products were identified by $^1$H and $^{19}$F NMR spectra taken on a 250 MHz instrument as compared to the same fluorided metallocene obtained by fluoriding using $(Bu)_3SnF$ reagents as is known in the art.

Example 1

Synthesis of $[Me_2Si(H_4Ind)_2]ZrF_2$

Method A. A 3.0 M solution of MeMgBr ("Me" is methyl) in Et2O (2.9 mL, 8.7 mmol) was added dropwise by syringe to a suspension of $[Me_2Si(H_4Ind)_2]ZrCl_2$ (2.00 g, 4.38 mmol) in $Et_2O$ (40 mL) and stirred at room temp. for 18 h. The volatiles were removed under reduced pressure and the residue was extracted with pentane (80 mL). The extract was filtered through a fritted glass filter and neat $BF_3.OEt_2$ (0.62 g, 4.4 mmol) was added dropwise by pipette to the stirring solution. After stirring at room temp. for 18 h, the precipitated solid was collected on a flitted glass filter and washed with cold pentane (20 mL). The residual solvent was removed under reduced pressure leaving 1.24 g (2.93 mmol, 67%) of a light tan solid. The compound was identified by comparison of its $^1$H and $^{19}$F NMR spectra to those of a reference sample. Method B. The procedure of Method A was repeated except that MeMgBr was replaced by a 1.4 M solution of MeLi in $Et_2O$ (6.3 mL, 8.8 mmol). The product was obtained as a light tan solid (1.03 g, 2.43 mmol, 55%). The compound was identified by comparison of its $^1$H and $^{19}$F NMR spectra to those of a reference sample of fluorided metallocene.

Example 2

Synthesis of $(BuC_5H_4)_2ZrF_2$

A 3.0 M solution of MeMgBr in $Et_2O$ (3.3 mL, 9.9 mmol) was added dropwise by syringe to a suspension of $(BuC_5H_4)_2 ZrCl_2$ (2.00 g, 4.94 mmol) ("Bu" is butyl) in $Et_2O$ (50 mL) and stirred at room temp. for 18 h. The volatiles were removed under reduced pressure and the residue was extracted with pentane (70 mL). The extract was filtered through a fritted glass filter and neat $BF_3.OEt_2$ (0.70 g, 4.9 mmol) was added dropwise by pipette to the stirring solution. After stirring at room temp. for 18 h, the clear solution was decanted away from an oily residue and concentrated under reduced pressure. The precipitate that formed was collected on a fritted glass filter and washed with cold pentane (10 mL). Residual solvent was removed under reduced pressure leaving 0.66 g (1.8 mmol, 36%) of a white solid. The compound was identified by comparison of its $^1$H and $^{19}$F NMR spectra to those of a reference sample of fluorided metallocene.

Example 3

Synthesis of $(1,3-Bu,MeC_5H_3)_2ZrF_2$

A 3.0 M solution of MeMgBr in $Et_2O$ (3.1 mL, 9.3 mmol) was added dropwise by syringe to a suspension of $(1,3-Bu,MeC_5H_3)_2ZrCl_2$ (2.00 g, 4.62 mmol) in $Et_2O$ (50 mL) and stirred at room temp. for 18 h. The volatiles were removed under reduced pressure and the residue was extracted with pentane (60 mL). The extract was filtered through a fritted glass filter and neat $BF_3.OEt_2$ (0.66 g, 4.7 mmol) was added dropwise by pipette to the stirring solution. After stirring at room temp. for 18 h, the slightly cloudy solution was filtered through a fritted glass filter and concentrated down to a thick slurry under reduced pressure. The solid was collected on a fritted glass filter and washed with cold pentane (10 mL). Residual solvent was removed under reduced pressure leaving 1.06 g (2.65 mmol, 57%) of a white solid. The compound was identified by comparison of its $^1$H and $^{19}$F NMR spectra to those of a reference sample of fluorided metallocene.

Example 4

Synthesis of $(PrC_5H_4)_2HfF_2$

Method A. A 3.0 M solution of MeMgBr in $Et_2O$ (2.9 mL, 8.7 mmol) was added dropwise by syringe to a suspension of $(PrC_5H_4)_2HfCl_2$ (2.00 g, 4.31 mmol) in $Et_2O$ (50 mL) and stirred at room temp. for 18 h. The volatiles were removed under reduced pressure and the residue was extracted with pentane (60 mL). The extract was filtered through a fritted glass filter and neat $BF_3.OEt_2$ (0.61 g, 4.3 mmol) was added dropwise by pipette to the stirring solution. After stirring at room temp. for 18 h, the slightly cloudy solution was filtered through a fritted glass filter and concentrated to 10 mL under reduced pressure. The precipitate that formed was collected on a fritted glass filter and washed with cold pentane (10 mL). Residual solvent was removed under reduced pressure leaving 1.12 g (2.60 mmol, 60%) of a white solid. The compound was identified by comparison of its $^1$H and $^{19}$F NMR spectra to those of a reference sample. Method B. The procedure of Method A was used except that $BF_3.THF$ (0.60 g, 4.3 mmol) was used as the fluorinating agent. The yield of product was 1.20 g (2.79 mmol, 65%). Method C. To a solution of $(PrC_5H_4)_2HfMe_2$ (2.00 g, 4.73 mmol) in pentane (60 mL) was added $BF_3.OEt_2$ (0.45 g, 3.2 mmol) dropwise by pipette. The slightly cloudy mixture was stirred at room temp. for 18 h and then filtered through a fritted glass filter. The solution was concentrated to 10 mL under reduced pressure and the resulting precipitate was collected on a fritted glass filter and washed with cold pentane (10 mL). The residual solvent was removed under reduced pressure leaving 1.29 g (2.99 mmol, 63%) of product. The compounds were identified by comparison of its $^1$H and $^{19}$F NMR spectra to those of a reference sample of fluorided metallocene.

Example 5

Synthesis of $(2-MeInd)_2ZrF_2$

To a solution of $(2-MeInd)_2ZrMe_2$ (1.46 g, 3.85 mmol) in pentane (60 mL) was added $BF_3.OEt_2$ (0.55 g, 3.9 mmol) dropwise by pipette. A precipitate immediately began to form and the mixture was stirred at room temp. for 18 h. The precipitate was collected on a fritted glass filter and washed with cold pentane (2×10 mL) and room temp. pentane (30 mL). Residual solvent was removed under reduced pressure leaving 1.37 g (3.53 mmol, 92%) of a light yellow powder. $^1$H NMR $(CD_2Cl_2)$: δ 1.88 (s, 6H, Me), 5.78 (s, 4H, cyclopentadienyl ring), 7.26 (m, 4H, aryl ring), 7.64 (m, 4H, aryl ring). $^{19}$F NMR: δ 51.1.

Comparative Example 1

A mixture of $BF_3.OEt_2$ (0.61 g, 4.3 mmol) and pentane (5 mL) was added by pipette to a partially dissolved sample of $(PrC_5H_4)_2HfCl_2$ (1.00 g, 2.16 mmol) in pentane (50 mL). The mixture was stirred at room temp. for 18 h and then filtered through a fritted glass filter and concentrated to 25 mL under reduced pressure. The precipitate that formed was collected on a fritted glass filter and residual solvent was removed under reduced pressure. The solid was identified by $^1$H NMR as unreacted $(PrC_5H_4)_2HfCl_2$ (0.79 g).

Comparative Example 2

A solution of $BF_3.OEt_2$ (0.44 g, 3.1 mmol) in $Et_2O$ (5 mL) was added by pipette to a solution of $(PrC_5H_4)_2HfCl_2$ (0.72 g, 1.6 mmol) in $Et_2O$ (30 mL). The solution was stirred at room temp. for 18 h and then the volatiles were removed under reduced pressure. The residue was extracted with pentane (70 mL) and filtered through a fritted glass filter. The solution was cooled to −25° C. and the precipitate that formed was collected on a flitted glass filter and the residual solvent was removed under reduced pressure. The solid was identified by $^1$H NMR as unreacted $(PrC_5H_4)_2HfCl_2$ (0.62 g).

Comparative Example 3

A 3.0 M solution of MeMgBr in $Et_2O$ (7.2 mL, 22 mmol) was added dropwise by syringe to a solution of $(PrC_5H_4)_2HfCl_2$ (5.00 g, 10.8 mmol) in $Et_2O$ (125 mL) and stirred at room temp. for 18 h. The mixture was filtered through a fritted glass filter and a solution $BF_3.OEt_2$ (3.07 g, 21.6 mmol) in $Et_2O$ (10 mL) was added dropwise by pipette to the stirring solution. After stirring at room temp. for 18 h, the volatiles were removed under reduced pressure and the residue was extracted with pentane (200 mL). The extract was filtered through a fritted glass filter and concentrated to 40 mL under reduced pressure. The precipitate that formed was collected on a fritted glass filter and washed with cold pentane (5 mL). The residual solvent was removed under reduced pressure. Concentration of the filtrate to 10 mL resulted in a second crop of solid. The combined yield was 0.95 g. The $^1$H NMR of the solid showed a mixture of products that did not correspond to either $(PrC_5H_4)_2HfCl_2$ or $(PrC_5H_4)_2HfF_2$.

Comparative Example 4

A 3.0 M solution of MeMgBr in $Et_2O$ (8.2 mL, 25 mmol) was added dropwise by syringe to a solution of $(BuC_5H_4)_2ZrCl_2$ (5.00 g, 12.4 mmol) in $Et_2O$ (125 mL) and stirred at room temp. for 18 h. The volatiles were removed under reduced pressure and the residue was extracted with pentane (150 mL). The extract was filtered through a fritted glass filter and a mixture of $BF_3.OEt_2$ (3.51 g, 24.7 mmol) and pentane (5 mL) was added dropwise by pipette to the stirring solution. After stirring at room temp. for 18 h, solid had formed on the flask walls. The liquid was decanted away and residual solvent was removed from the solid under reduced pressure. The remaining solution was concentrated to 20 mL and the resulting precipitate was isolated. The precipitate was recrystallized from pentane/toluene (2:1) at −25° C. giving off-white needle crystals. The crystals were washed with cold pentane (20 mL) and residual solvent was removed under reduced pressure. The combined yield of solid was 4.27 g. The $^1$H NMR spectra of both crops did not correspond to $(BuC_5H_4)_2ZrF_2$. Heating the solid under vacuum did not produce any change in the product.

The present invention offers several advantages over the prior art. Yields of fluorided catalyst component can range from 50% to greater than 90% in one embodiment, and from 55% to 80% a more particular embodiment. The fluorided catalyst component product is easily isolated, as it is typically a solid precipitate. Also, the present invention offers an economical approach to synthesizing fluorided catalyst components, as it is possible to select a fluoriding agent that is less expensive than prior art fluoriding agents.

Another advantage of the method of the present invention is the ease with which the fluorided catalyst component is isolated. In particular, since a non-coordinating diluent is used, in particular, a hydrocarbon diluent, the reaction byproduct can be removed without heating the product. The reaction between the alkylated catalyst component and fluoriding agent typically results in a byproduct that includes the corresponding alkylated-fluoriding agent. For example, when $BF_3$ is the fluoriding agent, and a methyl group is the alkyl leaving group bound to the alkylated catalyst component, the byproduct is $BF_2CH_3$ and/or $BF(CH_3)_2$. This must be separated from the desired fluorided catalyst component. In the present invention, the fluorided catalyst component tends to precipitate out from the non-coordinating diluent used while the alkylated fluoriding agent remains dissolved. Simple extraction and/or washing of the precipitate with the hydrocarbon solvent in which the reaction takes place will suffice in removing any remaining traces of residual fluoriding agent and other reaction products, without heating.

Thus, in one embodiment, the fluoridation reaction product is extracted with a hydrocarbon diluent at from less than 60° C., and in a more particular embodiment, extracted with a hydrocarbon diluent at from less than 50° C., and in a more particular embodiment, extracted with a hydrocarbon diluent at from less than 40° C., and in yet a more particular embodiment, extracted with a hydrocarbon diluent at from less than 30° C.

Yet another advantage of the present invention is the surprising ability to allow full and efficient fluoridation of the alkylated catalyst component (replacement of both leaving groups) with less than 2 equivalents of the fluoriding agent, or less than 3, or less than or equal to 1.5, equivalents of fluorine (as part of the fluoriding agent) per equivalent of leaving group bound to the metallocene metal center. For example, while the prior art discloses the use of $BF_3$, two or more equivalents of $BF_3$ are used for every one equivalent of metallocene. Examples 1–4 show the utility of using less than 3 equivalents of fluorine for every equivalent of leaving group.

In particular, Example 4, Method C, shows the utility of adding only 3.2 mmol fluoriding agent to 4.73 mmol alkylated metallocene, or about 0.7 equivalent fluoriding agent for every one equivalent alkylated metallocene, or about 1 equivalent of fluorine for every equivalent of non-halogen leaving group (methyl). This is in contrast to the comparative Example 4 where, even in pentane (a non-coordinating diluent), the use of two moles of fluoriding agent per mole of metallocene (or about 3 moles fluorine per mole non-fluorine leaving group) leads to products not corresponding to the desired difluorided metallocene. Further, the prior art discloses the use of 3 equivalents of fluorine (wherein there are three equivalents of fluorine per equivalent of etherate-$BF_3$) for every equivalent of leaving group. See W. W. Lukens, Jr. et al., 118 J. AM. CHEM. SOC. at 1726 (1996). Thus, the method of the present invention allows for the economical use of the fluoriding agent—a significant cost savings in bulk production of catalyst component.

To add to the economy of the method of the invention, the fluoriding agent may be added as a pure compound—not diluted or solublized in any diluent prior to reaction with the alkylated catalyst component. Thus, for example, neat $BF_3$ as a liquid, purchased as the diether, may be added directly to the agitated solution of alkylated catalyst component in non-coordinating diluent. Further, there is no need to either cool or heat the reaction, thus adding further to its economy and simplicity. Finally, to further add to the economy of the invention, the method allows for the use of relatively low cost fluoriding agents such as the Group 13 fluoriding agents or boron compounds, as compared to tin-based fluoriding agents commonly used in the art (e.g., (Bu)$_3$SnF).

As well, the method of the invention can be tailored to suit most any catalyst component for olefin polymerization and oligomerization. The fluorided catalyst components of the invention may be selected such that reactor fouling (sheeting, agglomeration, etc.) is reduced or eliminated. Desirably, the polymerization method includes a gas-phase or slurry process wherein sheeting, as indicated by, for example, a raise in the reactor wall temperature, is substantially absent. By "substantially absent", it is meant that, over at least a 8 day period of continuous reactor polymerization, there is no sheeting as indicated by a less than 5° C. increase in the reactor wall temperature.

The method of the invention is particularly suited for the fluoriding of alkylated metallocene catalyst components described in general as (Cp)$_r$MX$_n$; wherein Cp is cyclopentadienyl or group isolobal to cyclopentadienyl and may be substituted in any position, each Cp being bound to the metal center M; wherein r is 1 or 2; and wherein if r is 1, the Cp may be bridged to one or more X groups; and wherein if r is 2, the two Cp's may be bridged as described above; and wherein M is the metal center as defined above, and X is any non-halogen leaving group as defined above, each X being bound to the metal center M; and wherein n is 1 or 2. In a particular embodiment, each X is independently selected from methyl, phenyl, and benzyl.

Certain features of the present invention are described in terms of a set of numerical upper limits and a set of numerical lower limits. It should be appreciated that ranges formed by any combination of these limits are within the scope of the invention unless otherwise indicated.

Unless otherwise indicated, all numbers expressing quantities of ingredients, properties, reaction conditions, and so forth, used in the specification and claims are to be understood as approximations based on the desired properties sought to be obtained by the present invention, and the error of measurement, etc., and should at least be construed in light of the number of reported significant digits and by applying ordinary rounding techniques. Notwithstanding that the numerical ranges and values setting forth the broad scope of the invention are approximations, the numerical values set forth are reported as precisely as possible.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

What is claimed is:

1. A method of making a fluorided metallocene catalyst component comprising contacting in a non-coordinating diluent:
    (a) at least one fluoriding agent comprising fluorine; with
    (b) one or more alkylated metallocene catalyst components comprising one or more non-halogen leaving groups to produce a fluorided catalyst component, wherein the leaving group(s) provide for one carbon bond directly to the metal of the one or more metallocene catalyst components;
    wherein from less than 3 equivalents of fluorine are contacted for every equivalent of leaving group.

2. The method of claim 1, wherein the fluoriding agent is a compound or combination of compounds capable of forming a chemical bond between at least one fluorine atom and the metal center of an alkylated catalyst component.

3. The method of claim 1, wherein the fluoriding agent is selected from compounds comprising at least one atom of fluorine and one or more atoms selected from the group consisting of H, Li, Na, K, Ca, Ti, Zr, Sm, Nb, Ta, Mo, B, Al, Ga, Ge, Re, C, Si, Sn, N, P, O, S, F, Cl, I and Br.

4. The method of claim 1, wherein the fluoriding agent is selected from compounds comprising at least one atom of fluorine and one or more atoms selected from the group consisting of H, Li, Na, K, B, C, Si, N, P, O, S, F, Cl, I and Br.

5. The method of claim 1, wherein the fluoriding agent is selected from Group 13 fluoride compounds.

6. The method of claim 1, wherein the fluoriding agent is added as a neat composition.

7. The method of claim 1, wherein less than or equal to 2 equivalents of fluorine are contacted per equivalent of leaving group.

8. The method of claim 1, wherein less than or equal to 1.5 equivalents of fluorine are contacted per equivalent of leaving group.

9. The method of claim 1, wherein less than 2 equivalents of fluoriding agent are contacted per equivalent of alkylated catalyst component.

10. The method of claim 1, wherein the fluoriding agent is contacted with the alkylated catalyst component to produce a reaction product; wherein the reaction product is extracted with a hydrocarbon solvent at from less than 70° C. to yield the fluorided catalyst component.

11. The method of claim 10, wherein the non-coordinating diluent is a hydrocarbon diluent consisting essentially of carbon and hydrogen.

12. The method of claim 10, wherein the non-coordinating diluent is selected from the group consisting of C$_4$ to C$_{40}$ linear alkanes, branched alkanes, cyclic alkanes, C$_6$ to C$_{20}$ aromatic hydrocarbons, and mixtures thereof.

13. The method of claim 1, wherein the components are contacted at a temperature that is between 10° C. to 35° C.

14. The method of claim 1, wherein the components are contacted at a temperature that is between 15° C. and 30° C.

15. The method of claim 1, wherein the alkylated metallocene catalyst component is selected from alkylated metallocene catalyst components represented by:

$$Cp^A Cp^B MX_n \text{ or } Cp^A(A)Cp^B MX_n$$

wherein M is a Group 4, 5 or 6 atom:
    each X is bound to M and is an non-halogen leaving group, n is 1 or 2;
    $Cp^A$ and $Cp^B$ are each bound to M and are cyclopentadienyl or ligands isolobal to cyclopentadienyl;
    (A) is bound to each of $Cp^A$ and $Cp^B$ and is bridging group.

16. The method of claim 1, wherein the alkylated metallocene catalyst component comprises two non-halogen leaving groups.

17. The method of claim 16, wherein the one or more non-halogen leaving groups is independently selected from groups that provide for at least one bond between the metal center of the alkylated catalyst component and one or more of the group selected from Group 12 atoms, Group 13 atoms, Group 14 atoms, Group 15 atoms, and Group 16 atoms.

18. The method of claim 1, wherein the one or more non-halogen leaving groups are independently selected from the group consisting of C$_1$ to C$_{12}$ alkyls, C$_2$ to C$_{12}$ alkenyls, C$_6$ to C$_{12}$ aryls, C$_7$ to C$_{20}$ alkylaryls, substituted C$_1$ to C$_{12}$ alkyls, substituted $C_6$ to $C_{12}$ aryls, substituted $C_7$ to $C_{20}$ alkylaryls and $C_1$ to $C_{12}$ heteroatom-containing alkyls, $C_5$ to $C_{12}$ heteroatom-containing aryls and $C_6$ to $C_{12}$ heteroatom-containing alkylaryls.

19. The method of claim 1, wherein fluoriding agents comprising tin are substantially absent.

* * * * *